(12) United States Patent
Lee

(10) Patent No.: US 9,125,617 B2
(45) Date of Patent: Sep. 8, 2015

(54) X-RAY IMAGING APPARATUS AND X-RAY IMAGING SYSTEM

(71) Applicant: SAMSUNG ELECTRONICS CO., LTD., Suwon (KR)

(72) Inventor: Duhgoon Lee, Suwon (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 108 days.

(21) Appl. No.: 13/915,967

(22) Filed: Jun. 12, 2013

(65) Prior Publication Data
US 2013/0343521 A1  Dec. 26, 2013

(30) Foreign Application Priority Data
Jun. 20, 2012  (KR) .................. 10-2012-0066047

(51) Int. Cl.
  H05G 1/64    (2006.01)
  A61B 6/00    (2006.01)
  G06F 19/00   (2011.01)

(52) U.S. Cl.
  CPC ............. *A61B 6/482* (2013.01); *A61B 6/463* (2013.01); *A61B 6/469* (2013.01); *A61B 6/505* (2013.01); *A61B 6/5205* (2013.01); *A61B 6/5241* (2013.01); *A61B 6/563* (2013.01); *G06F 19/322* (2013.01); *A61B 6/4035* (2013.01); *A61B 6/4241* (2013.01)

(58) Field of Classification Search
  CPC ..... G01N 23/04; G01N 23/06; G01N 23/083; A61B 6/482; H04N 5/3205; G06T 5/50; G06T 7/0012; G06T 7/0081; G06T 2207/10116; G06T 2207/30004
  USPC .............. 378/62, 98.5, 98.8, 98.9, 98.11; 382/128, 130, 132
  See application file for complete search history.

(56) References Cited

U.S. PATENT DOCUMENTS

| 5,590,215 | A  | * | 12/1996 | Allen .................... 382/128 |
| 7,424,679 | B1 | * | 9/2008  | Lamer et al. ............. 715/737 |
| 2003/0215119 | A1 |  | 11/2003 | Uppaluri et al. |
| 2005/0041845 | A1 | * | 2/2005  | Payne ..................... 382/132 |
| 2008/0089584 | A1 |  | 4/2008  | VanMetter et al. |
| 2009/0161939 | A1 |  | 6/2009  | Wu et al. |

FOREIGN PATENT DOCUMENTS

EP   2 583 625   10/2012

OTHER PUBLICATIONS

Extended European Search Report issued Sep. 3, 2013 in corresponding European Application No. 13 17 2589.

* cited by examiner

*Primary Examiner* — Jurie Yun
(74) *Attorney, Agent, or Firm* — Staas & Halsey LLP

(57) ABSTRACT

An X-ray imaging apparatus displays a bone or soft tissue image of an X-ray image, which corresponds to a region selected by a user, thereby reducing a diagnosis time. In addition, an X-ray imaging system transmits a first energy X-ray image and a second energy X-ray image to a central image management system, and a user control apparatus receives the images from the central image management system and displays a bone or soft tissue image corresponding to the selected region, thereby reducing burden imposed on server capacity of the central image management system as well as reducing a diagnosis time.

48 Claims, 31 Drawing Sheets

X-RAY IMAGING APPARATUS AND X-RAY IMAGING SYSTEM

CROSS-REFERENCE TO RELATED APPLICATIONS

This application claims the benefit of Korean Patent Application No. 10-2012-0066047, filed on Jun. 20, 2012 in the Korean Intellectual Property Office, the disclosure of which is incorporated herein by reference.

BACKGROUND

1. Field

One or more embodiments relate to an X-ray imaging apparatus and an X-ray imaging system, which obtain an X-ray image of bones or soft tissues of an object using a plurality of X-rays with different energy levels.

2. Description of the Related Art

An X-ray imaging apparatus irradiates an object with X-rays and analyzes X-rays transmitted through the object to examine an internal structure of the object. X-ray transmittance may differ according to tissues constituting the object. Thus, the internal structure of the object may be imaged using an attenuation coefficient obtained by indicating the transmittance as a numeric value.

Recently, a method of forming an X-ray image by irradiating X-rays with different energy levels, but not by irradiating X-rays with the same energy level has been developed and various research thereon has been conducted.

In particular, a dual energy X-ray imaging apparatus sequentially irradiates to an object with first energy X-rays and second energy X-rays to capture a plurality of radiography images and extracts clear and separate bone and soft tissue images, that is, a bone image clearly indicating bones and a soft tissue image clearly indicating soft tissues, from the radiography images.

In this case, when the bone image and soft tissue image extracted from an entire X-ray image are displayed, it takes a long time for a user to diagnose a lesion. In addition, when the user wants to check a bone or soft tissue image corresponding to only a part that is suspected to have a lesion, the user's need is not satisfied by a generated image.

In addition, the X-ray imaging apparatus transmits the bone or soft tissue image together with a first energy X-ray image or a second energy X-ray image to a picture archiving & communication system (PACS), resulting in burden to server capacity of the PACS.

SUMMARY

Therefore, the foregoing described problems may be overcome and/or other aspects may be achieved by one or more embodiments of an X-ray imaging apparatus that displays a bone or soft tissue image of an X-ray image, which corresponds to a region selected by a user, thereby reducing a diagnosis time.

The foregoing described problems may be overcome and/or other aspects may be achieved by one or more embodiments of an X-ray imaging system in which a first energy X-ray image and a second energy X-ray image are transmitted to a central image management system, and a user control apparatus receives the images from the central image management system and displays a bone or soft tissue image corresponding to the selected region, thereby reducing burden imposed on server capacity of the central image management system as well as reducing a diagnosis time.

Additional aspects and/or advantages of one or more embodiments will be set forth in part in the description which follows and, in part, will be apparent from the description, or may be learned by practice of one or more embodiments of disclosure. One or more embodiments are inclusive of such additional aspects.

In accordance with one or more embodiments, an X-ray imaging apparatus may include an X-ray generator to generate X-rays and irradiate an object with the X-rays, an X-ray detector to detect X-rays irradiated from the X-ray generator and transmitted through the object, and a host device to generate and display a plurality of X-ray images from the detected X-rays and to display an image containing at least one of bone image information and soft tissue image information of the displayed X-ray image, the bone image information and soft tissue image information corresponding to a region selected by a user.

The X-ray detector may detect first energy X-rays and second energy X-rays, wherein the first energy X-rays and the second energy X-rays have different energy levels.

The host device may include an X-ray image generator to generate a first energy X-ray image from the first energy X-rays detected by the X-ray detector and to generate a second energy X-ray image from the second energy X-rays detected by the X-ray detector.

The host device may further include an image display unit to display at least one of the first energy X-ray image and second energy X-ray image generated by the X-ray image generator.

The host device may further include an image information extractor to extract separate bone and soft tissue images from the first energy X-ray image and the second energy X-ray image to extract bone image information or soft tissue image information.

The host device may further include an input unit to receive, from the user, selection of at least one region of the image displayed on the image display unit.

The image information extractor may extract bone image information or soft tissue image information corresponding to the region selected by the user.

The image display unit may display the bone image or soft tissue image corresponding to the region selected by the user, and the bone image may contain the bone image information generated by the image information extractor and the soft tissue image may contain the soft tissue image information generated by the image information extractor.

The input unit may receive selection of at least one of bones and soft tissues from the user, and the image information extractor may extract image information corresponding to the selection.

The image display unit may replace the selected region of the displayed X-ray image with an image containing image information extracted from the image information extractor and displays the selected region.

The image information extractor may further include an image controller to generate one image containing both the bone image information and soft tissue image information of the image information extracted by the image information extractor, the bone image information and soft tissue image information corresponding to the selected region, wherein the selected region is selected via the input unit, and the one image may include a bone region corresponding to the bone image information and a soft tissue region corresponding to the soft tissue image information.

The image controller may adjust the bone region and soft tissue region included in the one image to different brightness levels.

The image controller may map the bone region and soft tissue region included in the one image to different colors.

The image display unit may display the one image generated by the image controller.

The image display unit may replace the selected region of the displayed X-ray image with the one image generated by the image controller.

In accordance with one or more embodiments, an X-ray imaging system may include an X-ray imaging apparatus to transmit and receive an X-ray image to and from a central image management system, and a user control apparatus, wherein the X-ray imaging apparatus may irradiate an object with X-rays, may detect X-rays transmitted through an object to generate a plurality of X-ray images, and may transmit the X-ray images to the central image management system, and wherein the user control apparatus may receive the X-ray images from the central image management system, may display the X-ray images, and may display an image containing at least one of bone image information and soft tissue image information when a user inputs selection of at least one region of the displayed X-ray image, wherein the image containing at least one of the bone image information and the soft tissue image information may correspond to a region selected by the user.

The X-ray imaging apparatus may irradiate the object with a first energy X-ray and second energy X-ray having different energy levels, may detect the first and second energy X-rays, and may generate a first energy X-ray image from the first energy X-ray and a second energy X-ray image from the second energy X-ray.

The user control apparatus may include an image display unit to receive the first energy X-ray image and second energy X-ray image generated by the X-ray imaging apparatus and to display at least one of the first energy X-ray image and the second energy X-ray image.

The user control apparatus may further include an image information extractor to extract separate bone and soft tissue images from the first energy X-ray image and the second energy X-ray image to extract bone image information or soft tissue image information.

The user control apparatus may further include an input unit to receive, from the user, selection of at least one region of the image displayed on the image display unit.

The image information extractor may extract bone image information or soft tissue image information corresponding to the region selected by the user.

The image display unit may display the bone image or soft tissue image corresponding to the region selected by the user, and the bone image may contain the bone image information generated by the image information extractor and the soft tissue image containing the soft tissue image information generated by the image information extractor.

The input unit may receive selection of at least one of bones and soft tissues from the user, and the image information extractor may extract image information corresponding to the selection.

The image display unit may replace the selected region of the displayed X-ray image with an image containing image information extracted from the image information extractor and displays the selected region.

The image information extractor may further include an image controller to generate one image containing both the bone image information and soft tissue image information of the image information extracted by the image information extractor, the bone image information and soft tissue image information corresponding to the selected region, wherein the selected region is selected via the input unit, and the one image may include a bone region corresponding to the bone image information and a soft tissue region corresponding to the soft tissue image information.

The image controller may adjust the bone region and soft tissue region included in the one image to different brightness levels.

The image controller may map the bone region and soft tissue region included in the one image to different colors.

The image display unit may display the one image generated by the image controller.

The image display unit may replace the selected region of the displayed X-ray image with the one image generated by the image controller.

In accordance with one or more embodiments, a method of controlling an X-ray imaging apparatus may include generating a first energy X-ray image and second energy X-ray image having different energy levels; displaying at least one of the first energy X-ray image and the second energy X-ray image; receiving selection of at least one region of the displayed X-ray image; and generating and displaying an image containing at least one of bone image information and soft tissue image information corresponding to a region selected by a user.

The generating of the first energy X-ray image and second energy X-ray image may include extracting the bone image information or the soft tissue image information from the first energy X-ray image and the second energy X-ray image.

The generating of the first energy X-ray image and second energy X-ray image may include generating an image containing image information of the extracted bone image information or the soft tissue image information, the image information corresponding to the region selected by the user.

The generating of the first energy X-ray image and second energy X-ray image may include extracting the bone image information or soft tissue image information corresponding to the region selected by the user and generating an image containing the extracted bone image information or soft tissue image information.

The generating of the first energy X-ray image and second energy X-ray image may include extracting bone image information and soft tissue image information from the first energy X-ray image and the second energy X-ray image and generating one image containing bone image information and soft tissue image information of the extracted bone image information or soft tissue image information, the bone image information and soft tissue image information corresponding to the region selected by the user.

The generating of the first energy X-ray image and second energy X-ray image may include extracting bone image information and soft tissue image information corresponding to the region selected by the user from the first energy X-ray image and the second energy X-ray image and generating one image containing the extracted bone image information and soft tissue image information.

The method may further include adjusting a bone region and a soft tissue region to different brightness levels.

The method may further include mapping a bone region and soft tissue region included in the one image to different color channels.

In accordance with one or more embodiments, a method of controlling an X-ray imaging system including an X-ray imaging apparatus to generate an X-ray image and a user control apparatus may include the X-ray imaging apparatus generating a first energy X-ray image and second energy X-ray image having different energy levels and transmitting the first energy X-ray image and the second energy X-ray image to a central image management system, the user control apparatus receiving the first energy X-ray image and the second energy X-ray image from the central image management system and displaying at least one of the first energy X-ray image and the second energy X-ray image, receiving selection of at least one region of the displayed X-ray image, and generating and displaying at least one of bone image information and soft tissue image information corresponding to a region selected by a user.

The generating of the first energy X-ray image and second energy X-ray image may include extracting the bone image information or the soft tissue image information from the first energy X-ray image and the second energy X-ray image.

The generating of the first energy X-ray image and second energy X-ray image may include generating an image containing image information of the extracted bone image information or soft tissue image information, the image information corresponding to the region selected by the user.

The generating of the first energy X-ray image and second energy X-ray image may include extracting the bone image information or soft tissue image information corresponding to the region selected by the user and generating an image containing the extracted bone image information or soft tissue image information.

The generating of the first energy X-ray image and second energy X-ray image may include extracting bone image information and soft tissue image information from the first energy X-ray image and the second energy X-ray image and generating one image containing bone image information and soft tissue image information of the extracted bone image information or the soft tissue image information, the bone image information and soft tissue image information corresponding to the region selected by the user.

The generating of the first energy X-ray image and second energy X-ray image may include extracting bone image information and soft tissue image information corresponding to the region selected by the user from the first energy X-ray image and the second energy X-ray image and generating one image containing the extracted bone image information and soft tissue image information.

The method may further include adjusting a bone region and a soft tissue region to different brightness levels.

The method may further include mapping a bone region and soft tissue region included in the one image to different color channels.

BRIEF DESCRIPTION OF THE DRAWINGS

These and/or other aspects of the invention will become apparent and more readily appreciated from the following description of the embodiments, taken in conjunction with the accompanying drawings of which.

DETAILED DESCRIPTION

Figure 1:
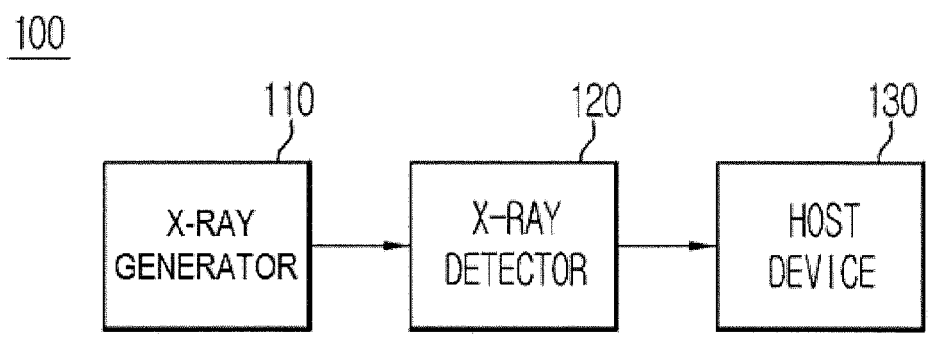
FIG. 1 is a control block diagram of an X-ray imaging apparatus according to one or more embodiments.

Reference will now be made in detail to one or more embodiments, illustrated in the accompanying drawings, wherein like reference numerals refer to like elements throughout. In this regard, embodiments of the present invention may be embodied in many different forms and should not be construed as being limited to embodiments set forth herein, as various changes, modifications, and equivalents of the systems, apparatuses and/or methods described herein will be understood to be included in the invention by those of ordinary skill in the art after embodiments discussed herein are understood. Accordingly, embodiments are merely described below, by referring to the figures, to explain aspects of the present invention.

Figure 2:
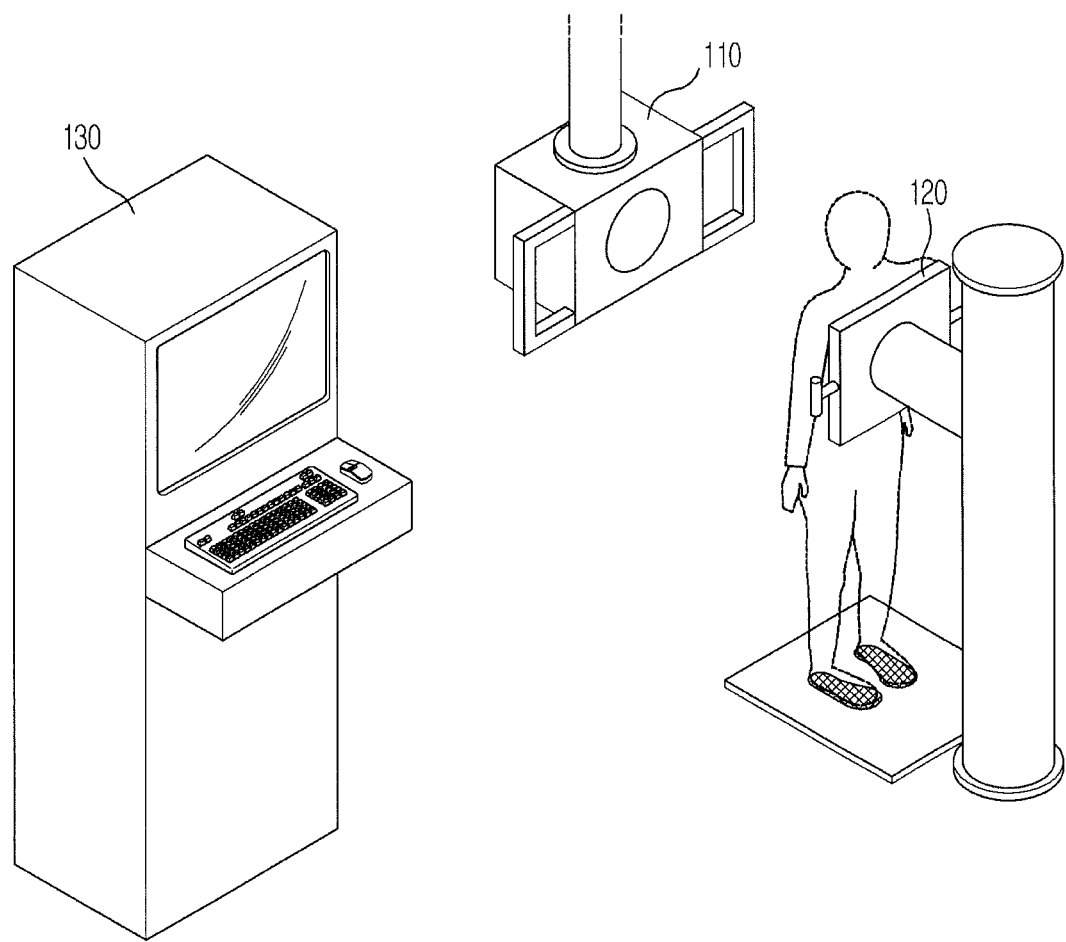
FIG. 2 is a diagram of an overall structure of an X-ray imaging apparatus, such as the X-ray imaging apparatus of FIG. 1.

FIG. 1 is a control block diagram of an X-ray imaging apparatus 100 according one or more embodiments and FIG. 2 is a diagram of an overall structure of an X-ray imaging apparatus, such as the X-ray imaging apparatus 100 of FIG. 1. As described below, the imaging apparatus uses X-rays to form images. However, other forms of electro-magnetic radiation may also be used.

Referring to FIGS. 1 and 2, the X-ray imaging apparatus 100 may include an X-ray generator 110 to generate X-rays and irradiate an object with the X-rays, an X-ray detector 120 to detect X-rays transmitted through the object, and a host device 130 to generate X-ray images using the detected X-rays.

The X-ray generator 110 may receive power from a power supply (not shown) to generate the X-rays and may irradiate the object with the X-rays. The X-ray generator 110 may generate X-rays which have an appropriate energy level to an examination target portion of the object, that is, an X-ray imaging portion. Energy and intensity of the irradiated X-rays may differ according to the power supplied from the power supply and an exposure time of the X-rays. In detail, the energy of the X-rays may be controlled according to an applied tube voltage, and the intensity or dose of the X-rays may be controlled according to tube current and the exposure time of the X-rays.

The X-ray generator 110 may irradiate monochromatic X-rays or polychromatic X-rays. According to one or more embodiments, the X-ray generator 110 may irradiate polychromatic X-rays having a predetermined energy band which is defined by an upper limit and a lower limit.

The upper limit of the energy band, that is, maximum energy of the irradiated X-rays may be controlled according to an amplitude of the tube voltage and the lower limit of the energy band, that is, minimum energy of the irradiated X-rays may be controlled by a filter that is installed inside or outside the X-ray generator 110. When X-rays in a low energy band are filtered by the filter, average energy of the irradiated X-rays may increase. Thus, an energy level of X-rays may be controlled by adjusting the energy band of the X-rays.

The X-ray detector 120 may detect the X-rays transmitted through the object. The X-rays irradiated by the X-ray generator 110 may pass through the object and may be attenuated while passing through the object. In this regard, transmittance of the X-rays may differ according to tissues constituting a portion to which the X-rays are irradiated, and thus, the amount of the transmitted X-rays may differ according to positions to which the X-rays are irradiated.

Tissues having different X-ray transmittances may be broadly classified, for example, into adipose tissue, soft tissue such as muscle and blood, tissue containing a large amount of calcium, such as bone and tooth, and gas. Thus, the amount of the transmitted X-rays may differ according to whether the X-rays are irradiated to bone, soft tissue, gas, or adipose tissue.

The X-ray detector 120 may detect the X-rays transmitted through the object, may convert the X-rays into an electric signal, and may transmit the electric signal to the host device 130. In this case, the X-ray detector 120 may detect a plurality of X-rays with different energy levels. In this regard, an example of a method of detecting a plurality of X-rays may include a method of separately irradiating a plurality of X-rays with different energy levels by the X-ray generator 110 and a method of extracting and detecting X-rays with a desired energy level by the X-ray detector 120.

In the former method, the X-ray generator 110 may separately generate and irradiates the X-rays with different energy levels, the X-ray detector 120 may detect the X-rays and may transmit the X-rays to the host device 130, and the host device 130 may form images of the X-rays via an image process. This method is well known in the art, and thus, a detailed description thereof is omitted here.

In the latter method, the X-ray generator 110 may irradiate X-rays once and the X-ray detector 120 which includes a photon counting detector (PCD) may divide the X-rays according to energy levels.

In detail, when the X-rays transmitted through the object reaches a photo diode region of the PCD, electrons in a valence band may receive photon energy of the X-rays sufficient to exceed a band gap energy difference and may be excited to a conduction band. Due to such excitation, a large amount of electron-hole pairs may be generated in a depletion region and moved by an electric field such that current flows. In this regard, the amount of the current may be detected to obtain data about intensity of X-rays that reach a pixel through the object. Then, a plurality of data of pixels may be collected to form one planar image.

The PCD may convert current according to flow of the electron-hole pairs generated whenever photons corresponding to energy of the X-rays are incident on the PCD into a voltage signal, may amplify the voltage signal, and may input the amplified voltage signal to a comparer. The comparer may compare the amplified voltage signal with a reference voltage to output a pulse. A counter may count the output pulse of the comparer per unit time to measure the intensity of the incident X-rays.

According to one or more embodiments, a method of detecting X-rays with different energy levels is not particularly limited. Thus, the above-described two methods may be used and other methods may also be used.

The number of the different energy levels is not limited. However, hereinafter, for convenience of description, a case in which X-rays with two different energy levels are detected will be described.

The host device 130 may generate the X-ray images using an X-ray signal detected by the X-ray detector 120 and may display at least one of the X-ray images.

In detail, when the X-rays with different energy levels are respectively referred to as a first energy X-ray and a second energy X-ray, the host device 130 may generate a first energy X-ray image using the first energy X-ray and may generate a second energy X-ray image using the second energy X-ray.

In addition, the host device 130 may display at least one of the first energy X-ray image and the second energy X-ray image and may display a bone or soft tissue image corresponding to a region that is selected by a user from the displayed X-ray image. Here, the bone image and the soft tissue image may be separated from each other and extracted from the displayed X-ray image.

The overall structure shown in FIG. 2 is a just one exemplary embodiment. X-ray imaging may be performed when the object lies down or sits down. The present embodiment is not limited to the positions of elements shown in FIG. 2 so long as the X-ray imaging apparatus 100 includes elements that perform the above-described functions.

Hereinafter, an operation of the host device 130 will be described in detail.

Figure 3:
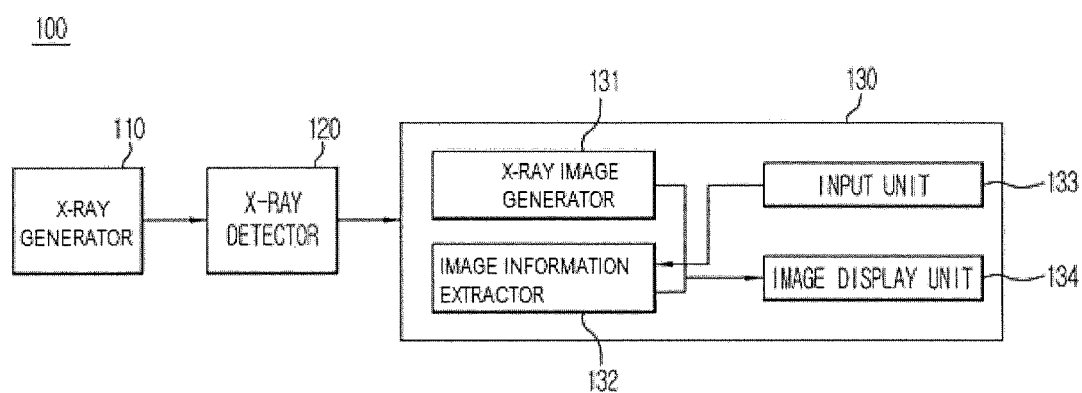
FIG. 3 is a control block diagram showing a detailed structure of a host device, such as the host device of the X-ray imaging apparatus of FIG. 1.

FIG. 3 is a control block diagram showing a detailed structure of a host device, such as the host device 130 of the X-ray imaging apparatus 100 of FIG. 1.

Referring to FIG. 3, the host device 130 may include an X-ray image generator 131 to generate the X-ray images based on the detected X-ray signal, an image information extractor 132 to extract image information about bones and soft tissues from the X-ray image, an input unit 133 to receive user selection, and an image display unit 134 to display the generated images.

The X-ray image generator 131 may generate the X-ray images by image processing the X-ray signal detected by the X-ray detector 120. In detail, the X-ray image generator 131 may generate the first energy X-ray image from a first energy X-ray signal and may generate the second energy X-ray image from a second energy X-ray signal. An image processing technique utilized by the X-ray image generator 131 may be one of well known image processing techniques used to generate an X-ray image.

The image display unit 134 may display at least one of the first energy X-ray image and the second energy X-ray image that are generated by the X-ray image generator 131. According to one or more embodiments, the image display unit 134 may display a high energy X-ray image of the two images. When two X-ray images with different levels are generated, one may be a high energy X-ray image and the other one may be a low energy X-ray image. An X-ray image that is more easily analyzed may vary according to a diagnosis target. For example, when the diagnosis target is a chest, a high energy X-ray image may be displayed. With regard to breasts, a low energy X-ray image may be displayed. In addition, it may be possible to display both the high energy X-ray image and the low energy X-ray image.

The image information extractor 132 may extract bone images and soft tissue images from the first energy X-ray image and the second energy X-ray image to extract bone image information about a bone or soft tissue image information about a soft tissue. Here, bone is in contrast to soft tissue and may include calcified hard tissues and the like in addition to a bone of a body.

In detail, the image information extractor 132 may extract the bone image information and the soft tissue image information from the first energy X-ray image and the second energy X-ray image, respectively, using an attenuation characteristic difference therebetween.

The transmittance or attenuation rate of X-rays varies according to a material through which they pass. An X-ray image indicates an internal structure of the object using this characteristic. The bone and the soft tissue have different transmittances with respect to X-rays of the same energy level. In this case, when an energy level of the X-rays is changed, a transmittance difference between the bone and the soft tissue is changed.

The image information extractor 132 may extract the bone image information which indicates the bone by reducing a residual image of the soft tissue of the X-ray images or the soft tissue information which indicates the soft tissue by reducing a residual image of the bone of the X-ray images, using the transmittance characteristic or attenuation characteristic of the bone and soft tissue.

In addition, the image information extractor 132 may generate the bone image containing the bone image information or the soft tissue image containing the soft tissue image information. Here, the bone image indicates the bone by reducing the residual image of the soft tissue and the soft tissue image indicates the soft tissue by reducing the residual image of the bone.

According to one or more embodiments, in order to extract the bone image information or the soft tissue image information, dual energy X-ray absoptiometry (DEXA), which is well known, may be used. The DEXA is a method of extracting image information clearly indicating a desired portion of bone and soft tissue by extracting images from high energy X-rays and low energy X-rays, logarithmically expressing the images, applying appropriate weights to the images, and then obtaining a difference therebetween.

However, the DEXA is just one image information extraction algorithm that may be used by the image information extractor 132. Thus, the image information extractor 132 may apply various algorithms to extract the bone image information or the soft tissue image information.

The input unit 133 may receive user selection of at least one region of the X-ray image on the image display unit 134. The input unit 133 may be embodied, for example, by any one of a mouse, a trackball, a keyboard, and a touch pad, etc. When the image display unit 134 is embodied as a touchscreen, for example, the touchscreen may function as both the input unit 133 and the image display unit 134.

When the user selection is input to the input unit 133, the image display unit 134 may display a portion of the bone image or soft tissue image, which corresponds to the selected region.

Hereinafter, operations of the image display unit 134 and the image information extractor 132 according to the user selection will be described.

Figure 4A:
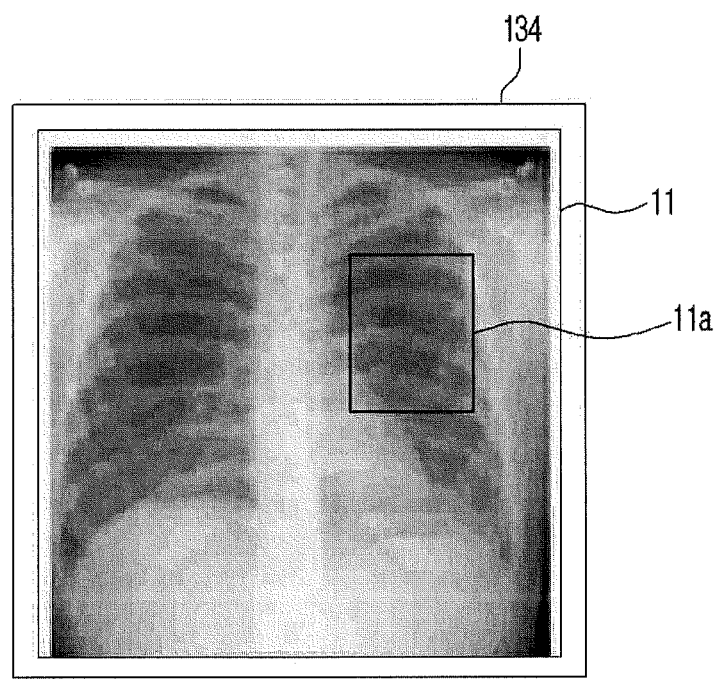
FIG. 4A shows a first energy X-ray image displayed on an image display unit according to one or more embodiments.
Figure 4B:
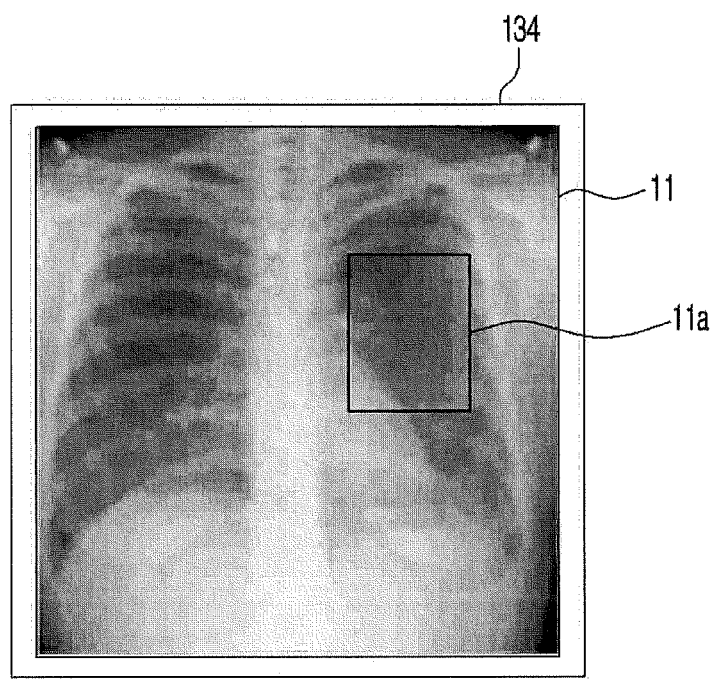
FIG. 4B shows a bone image displayed according to user selection according to one or more embodiments.
Figure 4C:
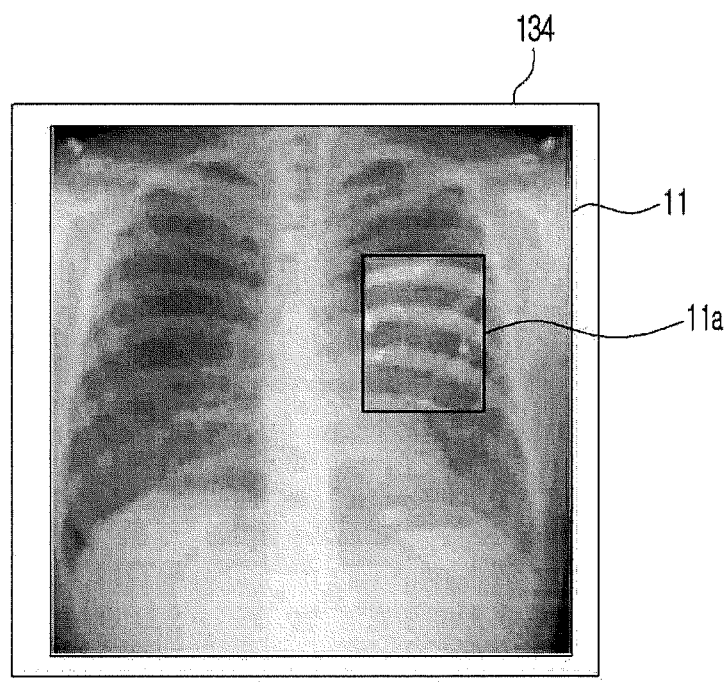
FIG. 4C shows a soft tissue image displayed according to user selection according to one or more embodiments.

FIGS. 4A to 4C are diagrams showing images displayed on the image display unit 134, according to one or more embodiments. FIG. 4A shows a first energy X-ray image 11 displayed on an image display unit, such as the image display unit 134, FIG. 4B shows a bone image displayed according to user selection, and FIG. 4C shows a soft tissue image displayed according to user selection.

As shown in FIG. 4A, the first energy X-ray image 11 generated by the X-ray image generator 131 may be displayed on the image display unit 134. According to one or more embodiments, first energy may be high energy. When the first energy X-ray image 11 is displayed on the image display unit 134, a user, that is, an inspector may analyze the first energy X-ray image 11 to perform diagnosis.

The user may find a region that is suspected to have a lesion during the diagnosis through the first energy X-ray image 11. In this case, the input unit 133 may receive user selection of a corresponding region from the user. As shown in FIG. 4A, a selected region 11a may have a predetermined area. When the input unit 133 is embodied, for example, as a mouse, a trackball, a keyboard, a touch pad, or the like, the user may manipulate the input unit 133 to input user selection of at least one region of the X-ray image displayed on the image display unit 134. When the input unit 133 and the image display unit 134 are embodied, for example, as a touchscreen, the user may directly touch a desired region of the X-ray image displayed on the touchscreen to input the user selection.

The image information extractor 132 may perform operations corresponding to one or more embodiments. Primarily, when the user selection is input through the input unit 133, the image information extractor 132 may extract bone image information or soft tissue image information of the selected region 11a only and may generate an image containing the extracted information. Secondly, the image information extractor 132 may extract bone image information or soft tissue image information of an entire portion of the first energy X-ray image 11 regardless of the user selection and then may generate a bone or soft tissue image of the selected region 11a only when the user selection is input to the input unit 133.

As shown in FIG. 4B, the image display unit 134 may display the bone image corresponding to the selected region 11a. Alternatively, as shown in FIG. 4C, the image display unit 134 may display the soft tissue image corresponding to the selected region 11a.

As shown in FIGS. 4B and 4C, when the bone image or the soft tissue image replaces the selected region 11a of the first energy X-ray image 11 displayed on the image display unit 134 and is displayed, the user may recognize a position of the region that is suspected have a lesion and a relationship with other regions during the diagnosis.

Figure 5A:
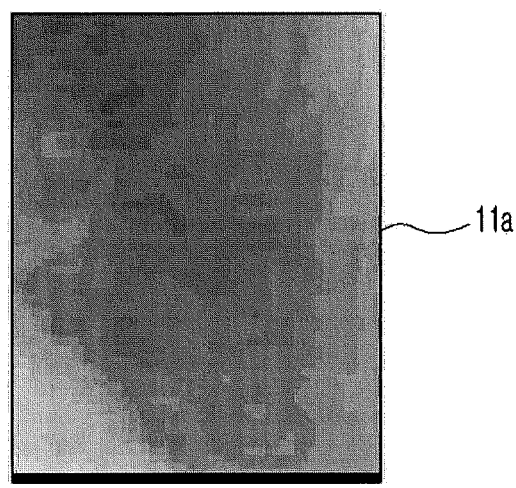
FIGS. 5A and 5B are diagrams showing images displayed on an image display unit, according to one or more embodiments.
Figure 5B:
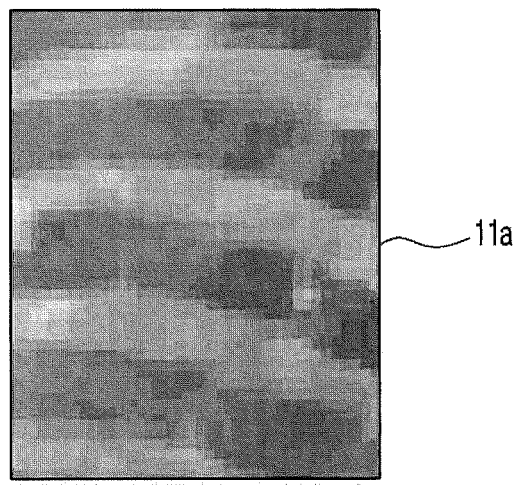

FIGS. 5A and 5B are diagrams showing images displayed on an image display unit, such as the image display unit 134, according to one or more embodiments.

As described with reference to FIG. 4A, the first energy X-ray image 11 may be displayed on the image display unit 134. When user selection is input through the input unit 133, the image display unit 134 may replace an entire portion of the first energy X-ray image 11 with a bone or soft tissue image corresponding to the selected region 11a and may display the bone or soft tissue image, as shown in FIGS. 5A and 5B. In this case, a region that is suspected to have a lesion is enlarged to possibly facilitate diagnosis of the region that is suspected to have the lesion.

The input unit 133 may also receive user selection about whether the bone image or soft tissue image of the selected region 11a is to be displayed. When the display of the soft tissue image is selected, the soft tissue image corresponding to the selected region 11a may be displayed, as shown in FIGS. 4B and 5A. When the display of the bone image is selected, the bone image corresponding to the selected region 11a may be displayed, as shown in FIGS. 4C and 5B.

The input unit 133 may also receive user selection of the size of the bone image or soft tissue image corresponding to the selected region 11a. In this case, the image display unit 134 may display the bone image or soft tissue image of which the size is adjusted according to the user selection.

Hereinafter, an X-ray imaging apparatus according to one or more embodiments will be described.

Figure 6:
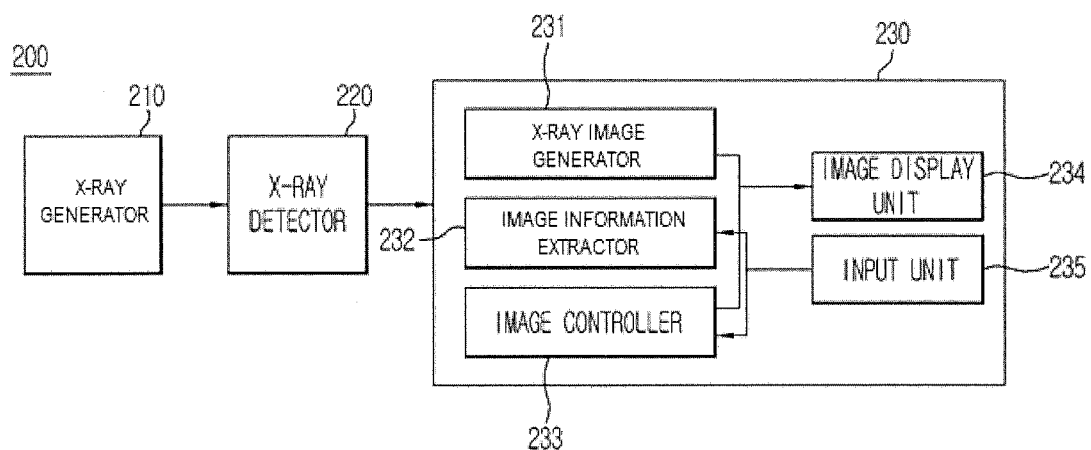
FIG. 6 is a control block diagram of an X-ray imaging apparatus according to one or more embodiments.

FIG. 6 is a control block diagram of an X-ray imaging apparatus, such as X-ray imaging apparatus 200 according to one or more embodiments.

Referring to FIG. 6, the X-ray imaging apparatus 200 may include an X-ray generator 210, an X-ray detector 220, and a host device 230. In addition, the host device 230 may include an X-ray image generator 231 to generate an X-ray image, an image information extractor 232 to extract bone and soft tissue image information from the X-ray image, an input unit 235 to receive user selection, and an image display unit 234 to display the X-ray image.

The host device 230 of the X-ray imaging apparatus 200 may further include an image controller 233 to generate one image containing both the bone image information and the soft tissue image information. Hereinafter, an operation of the image controller 233 will be described in detail.

When a user analyzes a region that is suspected to have a lesion, an image indicating soft tissues only or an image indicating bones only may be useful, but an image indicating both the bones and the soft tissues may be used to check a relationship between the bones and the soft tissues.

Thus, the image information extractor 232 of the X-ray imaging apparatus 200 may extract both the bone image information indicating bones and the soft tissue image information indicating the soft tissues, and the image controller 233 may generate one image containing both the bone image information and the soft tissue image information and may output the one image on the image display unit 234.

Also, the X-ray imaging apparatus 200 may extract image information about only the selected region and display the one image or alternatively may extract image information regardless of user selection and display the one image corresponding to the selected image only.

Figure 7A:
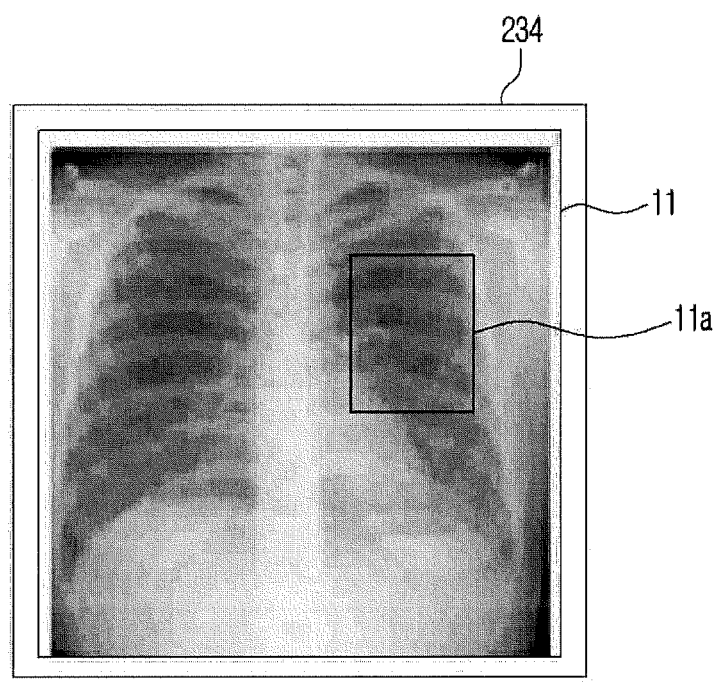
FIGS. 7A, 7B, and 7C are diagrams showing images displayed on an image display unit of an X-ray imaging apparatus, according to one or more embodiments.
Figure 7B:
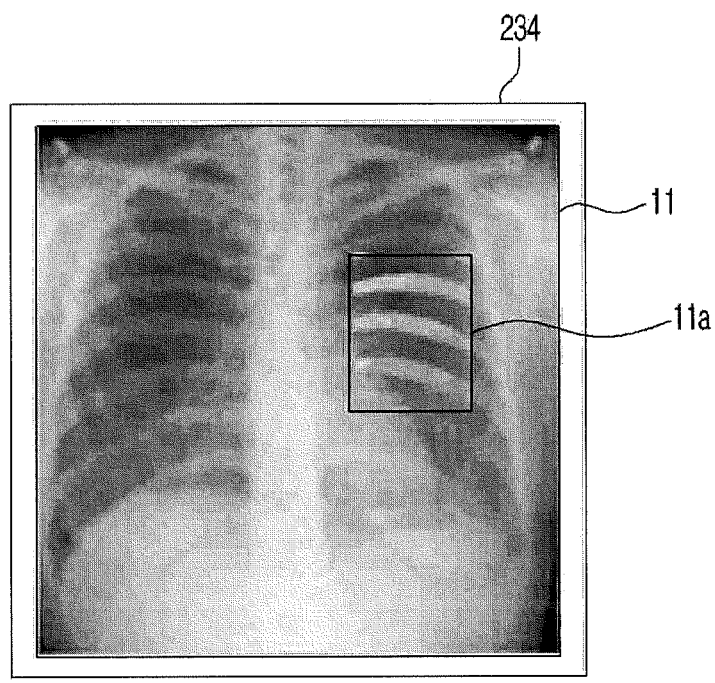
Figure 7C:
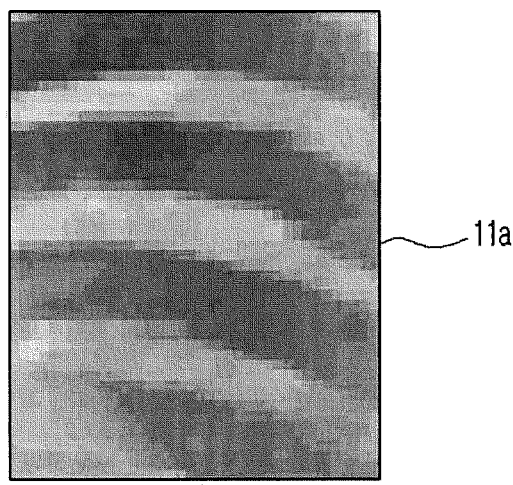

FIGS. 7A, 7B, and 7C are diagrams showing images displayed on an image display unit, such as the image display unit 234 of the X-ray imaging apparatus 200, according to one or more embodiments.

As shown in FIG. 7A, when a user selects at least one region, that is, the selected region 11a of the first energy X-ray image 11 displayed on the image display unit 234, an image corresponding to the selected region 11a may replace the selected region 11a and may be displayed, as shown in FIG. 7B. The image may contain both the bone image information and soft tissue image information of the selected region 11a, and that is, may indicate both the bones and soft tissues of the selected region 11a. In addition, as shown in FIG. 7C, the image containing both the bone image information and soft tissue image information of the selected region 11a may be enlarged and displayed on an entire portion of the image display unit 234.

In addition, when the image controller 233 generates the image containing the bone image information and the soft tissue image information, the image controller 233 may adjust bone and soft tissue regions of the image to different brightness levels such that the bones and the soft tissues may be distinguished from each other.

According to one or more embodiments, the image controller 233 may further include a brightness adjusting filter. The brightness adjusting filter may adjust pixel values corresponding to the bone or soft tissue region of the image containing the bone image information and the soft tissue image information such that the bone region and the soft tissue region may exhibit different brightness levels. In this case, a lighter region of the bone region and the soft tissue region may be optionally set by the image controller 233 or may be determined by user selection input to the input unit 235.

When the bone region is set to be lighter than the soft tissue region, the brightness of all pixels corresponding to the bone region of the one image containing the bone image information and the soft tissue image information may be multiplied by a predetermined value such that the bone region may be displayed lighter than the soft tissue region, which may be performed using the brightness adjusting filter.

When the soft tissue region is set to be lighter than the bone region, the brightness of all pixels corresponding to the soft tissue region of the one image containing the bone image information and the soft tissue image information may be multiplied by a predetermined value such that the soft tissue region may be displayed lighter than the bone region, which may be performed using the brightness adjusting filter.

According to one or more embodiments, any one of the bone region and the soft tissue region may be adjusted to be lighter or darker than the other such that the bone region and the soft tissue region may exhibit at different brightness levels. That is, the image controller 233 may adjust the bone region and the soft tissue region to be lighter or darker than each other.

In addition, when the image controller 233 generates the image containing the bone image information and the soft tissue image information, the image controller 233 may map the bone region and the soft tissue region to different color channels, respectively, so as to distinguish the bone image and the soft tissue image from each other.

The image controller 233 may map the bone image information and the soft tissue image information that are extracted from the image information extractor 232 to the different color channels, respectively. That is, the image controller 233 may map the bone region corresponding to the bone image information and the soft tissue region corresponding to the soft tissue image information to the different color channels, respectively.

In general, an X-ray image is presented in grayscale, that is, in black and white as opposed to color channels. However, according to one or more embodiments, the bone image information and the soft tissue image information may be mapped to the color channels so as to distinguish the bone image and the soft tissue image of one image from each other based on a color difference therebetween. According to one or more embodiments, any color model may be used such that the color model includes at least two colors, and thus, the type of the color model is not particularly limited.

For example, with regard to a red-green-blue (RGB) model, the image controller 233 may map the bone image information and the soft tissue image information to a red channel and a green channel, respectively, and may generate and output one image containing the bone image information and the soft tissue image information. Thus, the bone region and the soft tissue region of the one image may be displayed in red and green, respectively, so as to be distinguished from each other.

A portion of the image where the bones and the soft tissues overlap may be displayed in a mixed color of red and green. In this regard, when density of the bones is higher, red may be displayed more strongly. When density of the soft tissue is higher, green may be displayed more strongly.

The user may recognize how many degrees of the bones and the soft tissues exist in a corresponding portion through colors of the portion and may distinguish the bone and the soft tissues during the diagnosis.

Respective colors mapped to the bone image information and the soft tissue image information may be input through the input unit 235 and may be optionally set by the image controller 233.

Figure 8:
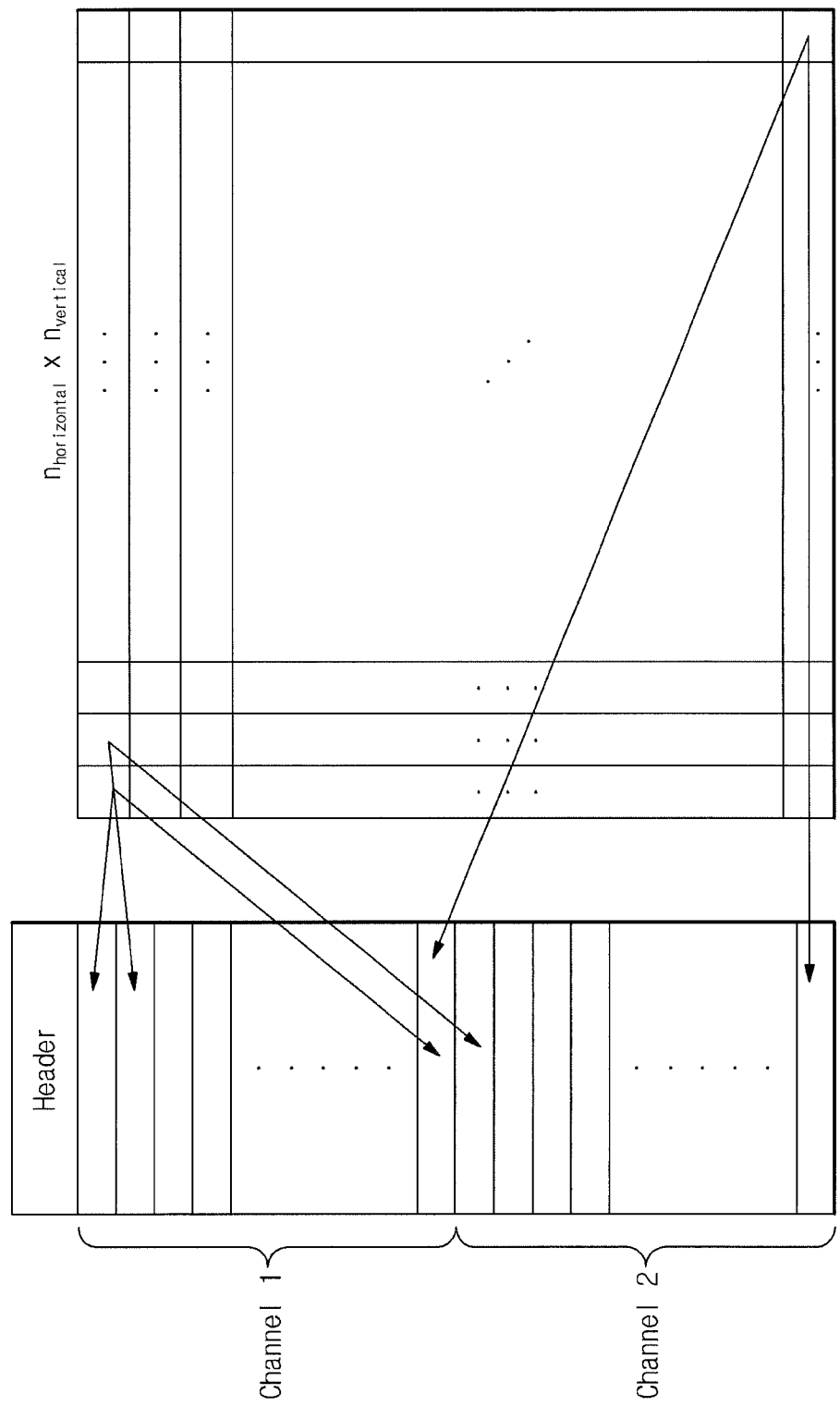
FIG. 8 is a schematic diagram of a data structure of one image generated by color mapping of an image controller according to one or more embodiments.

FIG. 8 is a schematic diagram of a data structure of one image generated by color mapping of an image controller according to one or more embodiments, such as the image controller 233.

Referring to FIG. 8, the one image containing the bone image information and the soft tissue image information may be divided into a plurality of pixels (n×n) each of which may contain bone image information and soft tissue information. Thus, when the bone image information and the soft tissue information are mapped to color channels CHANNEL 1 and CHANNEL 2 indicating different colors, image information of each pixel may be stored in a corresponding color channel, as shown in FIG. 8.

However, the data structure shown in FIG. 8 is just an example. A method of mapping the bone and soft tissue image information to color channels or a color mapping data structure is not limited to the above-described example.

In addition, the image controller 233 may perform color mapping on an entire region of the first energy X-ray image 11 and may display a selected region only, or alternatively, may perform the color mapping on the selected region only.

Figure 9:
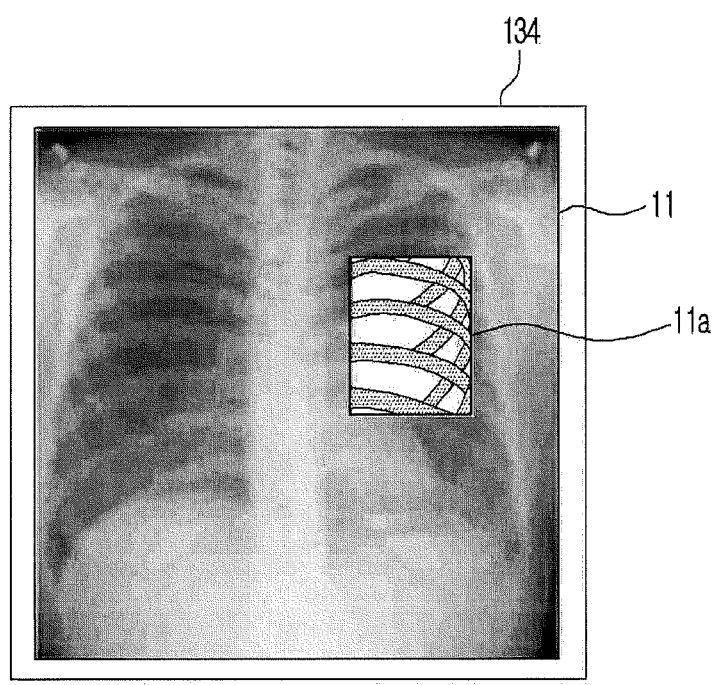
FIG. 9 is a schematic diagram of an image that is generated and displayed via color mapping of an image controller, according to one or more embodiments.

FIG. 9 is a schematic diagram of an image that is generated and displayed via color mapping of an image controller, such as the image controller 233, according to one or more embodiments. In the image shown in FIG. 9, bones are mapped to a red color denoted by dot patterns.

When a user selects at least one region, that is, the selected region 11a of the first energy X-ray image 11 displayed on the image display unit 234, the selected region 11a, which includes both the bone region and the soft tissue region, may be displayed. Here, the bone region and the soft tissue region may be replaced by images with different colors.

However, in the example illustrated by FIG. 9, the selected region 11a does not include the soft tissue region. Thus, only the bone region is indicated by the dot patterns in FIG. 9. In addition, the size of the selected region 11a may be enlarged according to user setting.

According to one or more embodiments, in the X-ray imaging apparatus 100 and 200, when the user selects a region that is suspected to have a lesion during diagnosis on a high energy X-ray image, the soft tissue image, the bone image, or the image containing both the soft tissue image and the bone image with respect to the selected region only may be output such that the user may perform the diagnosis.

Hereinafter, an X-ray imaging system will be described with regard to one or more embodiments.

Figure 10:
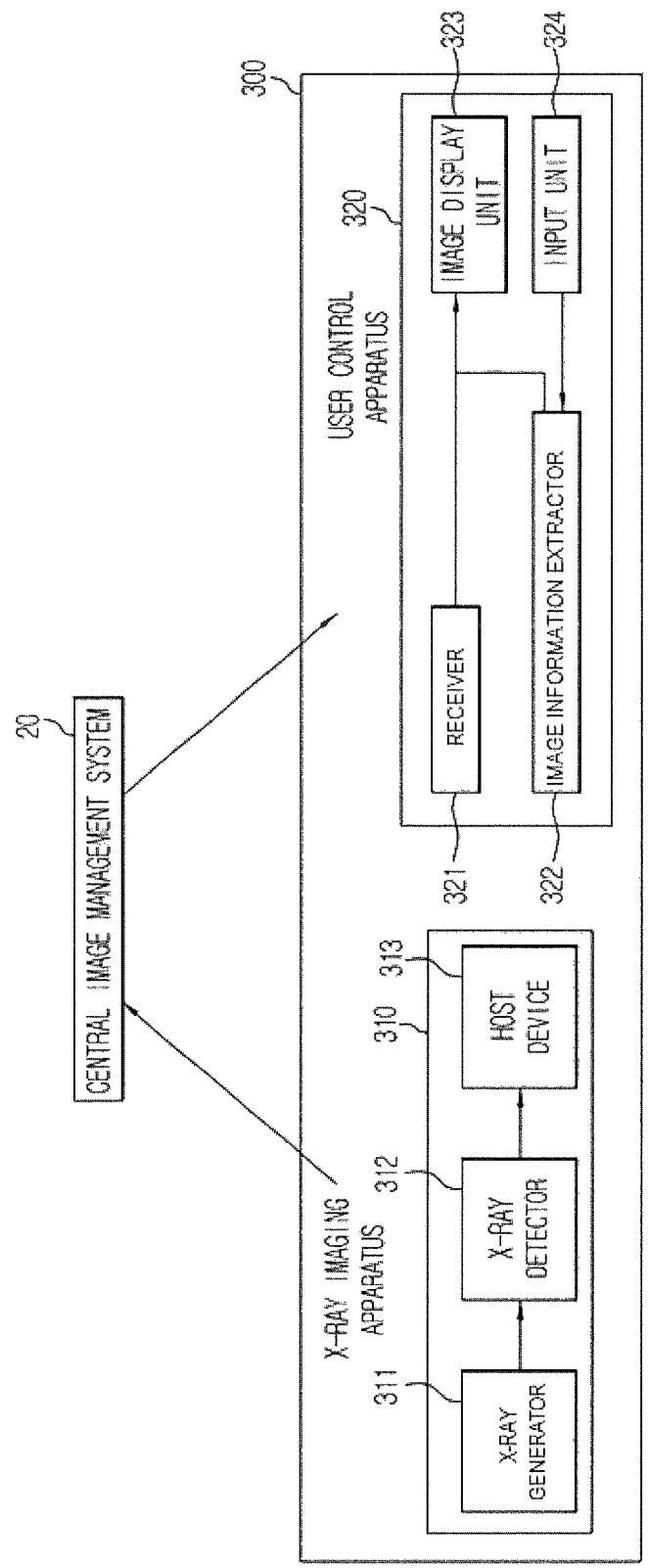
FIG. 10 is a control block diagram of an X-ray imaging system according to one or more embodiments.
Figure 11:
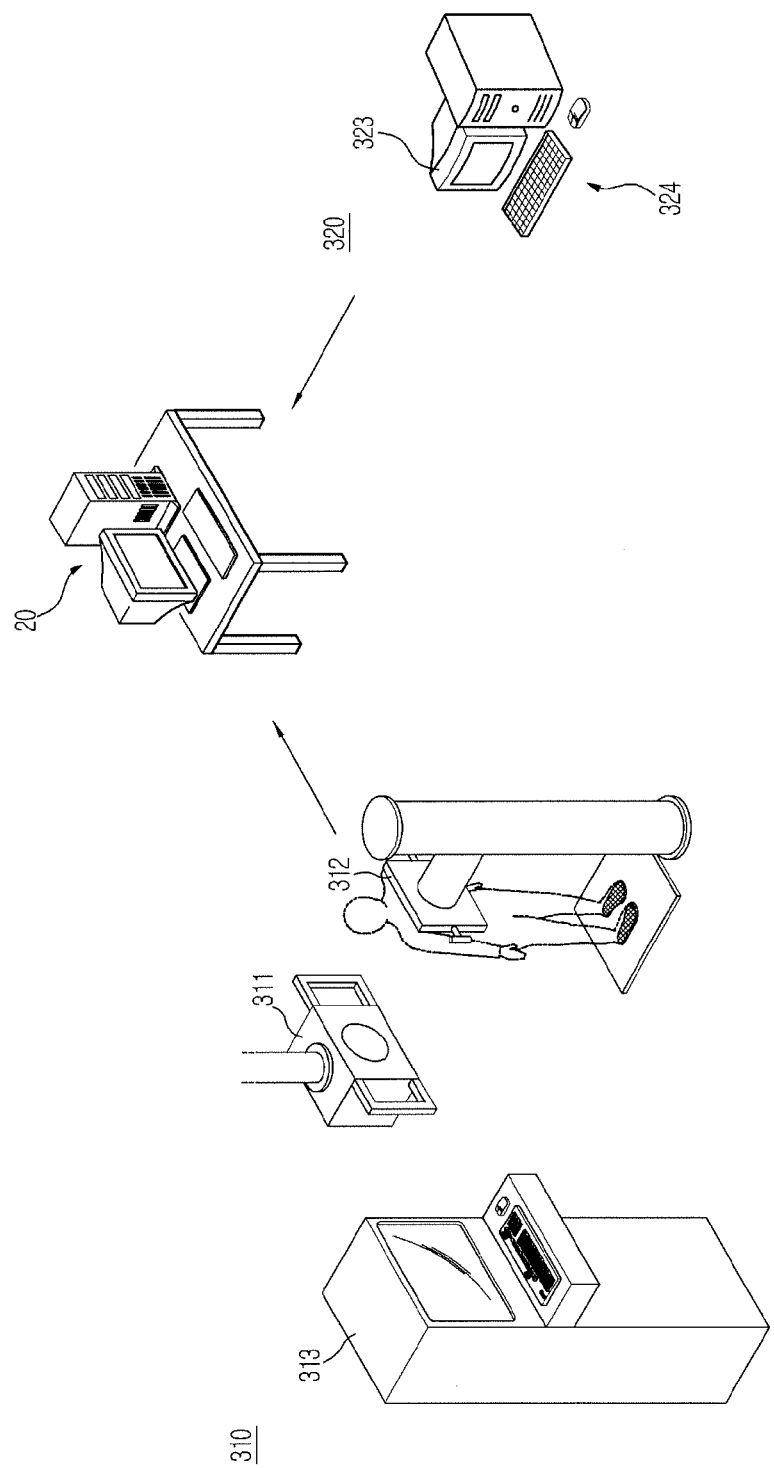
FIG. 11 is a diagram of an overall structure of the X-ray imaging system, such as the X-ray imaging system of FIG. 10.

FIG. 10 is a control block diagram of an X-ray imaging system 300 according to one or more embodiments and FIG. 11 is a diagram of an overall structure of an X-ray imaging system according to one or more embodiments, such as the X-ray imaging system 300 of FIG. 10.

Referring to FIGS. 10 and 11, the X-ray imaging system 300 may include an X-ray imaging apparatus 310 to generate a first energy X-ray image and a second energy X-ray image, and a user control apparatus 320 to extract bone image information and soft tissue image information from the first energy X-ray image and the second energy X-ray image.

In a medical institution such as a hospital or a health care center, for example, an X-ray image generated by the X-ray imaging apparatus 310 may be transmitted to and stored in a central image management system 20, that is, for example, a picture archiving & communication system (PACS), and a user downloads the X-ray image to the user control apparatus 320 such as a personal computer (PC) of the user from the PACS and analyzes the X-ray image to perform a diagnosis.

Conventionally, an X-ray imaging apparatus also generates separate bone and soft tissue images which are extracted from an X-ray image of an object and transmits the bone and soft tissue images to the PACS. However, in the X-ray imaging system 300 according to one or more embodiments, the X-ray imaging apparatus 310 may generate the first energy X-ray image and the second energy X-ray image and may transmit the first energy X-ray image and the second energy X-ray image to the central image management system 20. Then, the user control apparatus 320 may download the first energy X-ray image and the second energy X-ray image from the central image management system 20 and may generate a required bone or soft tissue image using the first energy X-ray image and the second energy X-ray image.

The X-ray imaging apparatus 310 may include an X-ray generator 311 to generate and irradiate X-rays, an X-ray detector 312 to detect the irradiated X-rays, and a host device 313 to generate an X-ray image using the detected X-rays.

The X-ray detector 312 may detect a plurality of X-rays with different energy levels. As described with reference to FIG. 1, a method of detecting a plurality of X-rays may include a method of separately irradiating a plurality of X-rays with different energy levels by the X-ray generator 311 and a method of extracting and detecting X-rays with a desired energy level by the X-ray detector 312.

The number of different energy levels is not particularly limited. Hereinafter, as only an example, two different energy levels are used and X-rays with the two different energy levels are referred to as a first energy X-ray and a second energy X-ray, respectively. Here, the first energy may be high energy and the second energy may be low energy or vice versa.

The host device 313 may generate the first energy X-ray image and the second energy X-ray image using an X-ray signal detected by the X-ray detector 312 and may transmit the first energy X-ray image and the second energy X-ray image to the central image management system 20.

The first energy X-ray image and the second energy X-ray image may be transmitted from the host device 313 directly to the user control apparatus 320.

The user control apparatus 320 may include a receiver 321 to receive the X-ray image, an image display unit 323 to display the X-ray image, an input unit 324 to receive user selection, and an image information extractor 322 to extract bone and soft tissue image information from the X-ray image.

The receiver 321 may receive the first energy X-ray image and the second energy X-ray image from the central image management system 20 or the X-ray imaging apparatus 310.

The image display unit 323 may display at least one of the first energy X-ray image and the second energy X-ray image. For example, the image display unit 323 may display a high energy X-ray image of the first energy X-ray image and the second energy X-ray image for image diagnosis.

The image information extractor 322 may extract the bone image information which indicates bones and the soft tissue image information which indicates soft tissues from the first energy X-ray image and the second energy X-ray image as in the image information extractor 132 of the X-ray imaging apparatus 100 described above with reference to FIG. 1.

The input unit 324 may receive the user selection of at least one region of the X-ray image displayed on the image display unit 323. When a user finds a portion suspected to have a lesion during the diagnosis of the X-ray image displayed on the image display unit 323, the user may specify and select that portion. The input unit 324 may be embodied, for example, as a mouse, a trackball, a touch pad, a keyboard, or the like. When the image display unit 323 is embodied as a touchscreen, for example, the touchscreen may perform functions of both the image display unit 323 and the input unit 324.

In addition, the input unit 324 may also receive user selection about whether the bone image or soft tissue image of a selected region is generated.

The image information extractor 322 may generate the bone or soft tissue image corresponding to the selected region and may display the bone or soft tissue image on the image display unit 323. Here, only the bone or soft tissue image information corresponding to the selected region may be extracted, or alternatively, the bone or soft tissue image information corresponding to the entire X-ray image may be extracted regardless of the user selection and then only the bone or soft tissue image corresponding to the selected region may be generated.

Figure 12A:
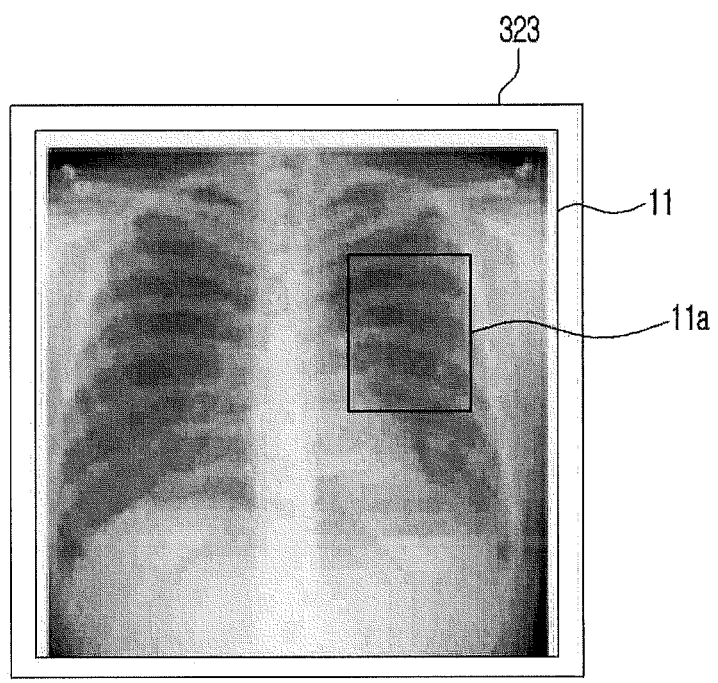
FIGS. 12A, 12B, and 12C are diagrams showing images displayed on an image display unit of a user control apparatus according to one or more embodiments.
Figure 12B:
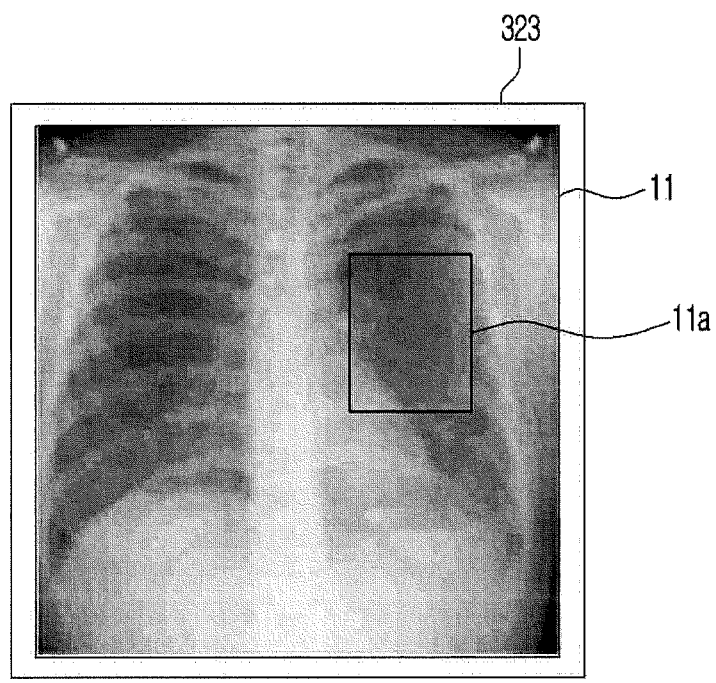
Figure 12C:
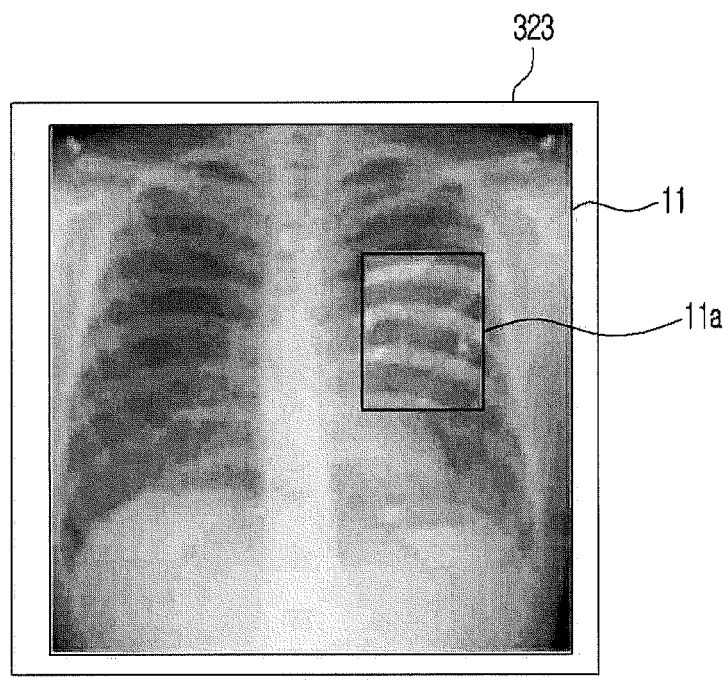

FIGS. 12A, 12B, and 12C are diagrams showing images displayed on an image display unit according to one or more embodiments, such as the image display unit 323 of the user control apparatus 320.

As shown in FIG. 12A, when the first energy X-ray image is displayed on the image display unit 323, the user may specify and select a desired region through the input unit 324. When the user selection is input, the bone or soft tissue image may replace the selected region and may be displayed, as shown in FIG. 12B. Alternatively, the bone or soft tissue image corresponding to the selected region 11a may replace the entire first energy X-ray image 11 and may be displayed, as shown in FIG. 12C.

User selection of the size of the bone or soft tissue image may be received through the input unit 324 and the bone or soft tissue image corresponding to the selected size may be displayed.

Figure 13:
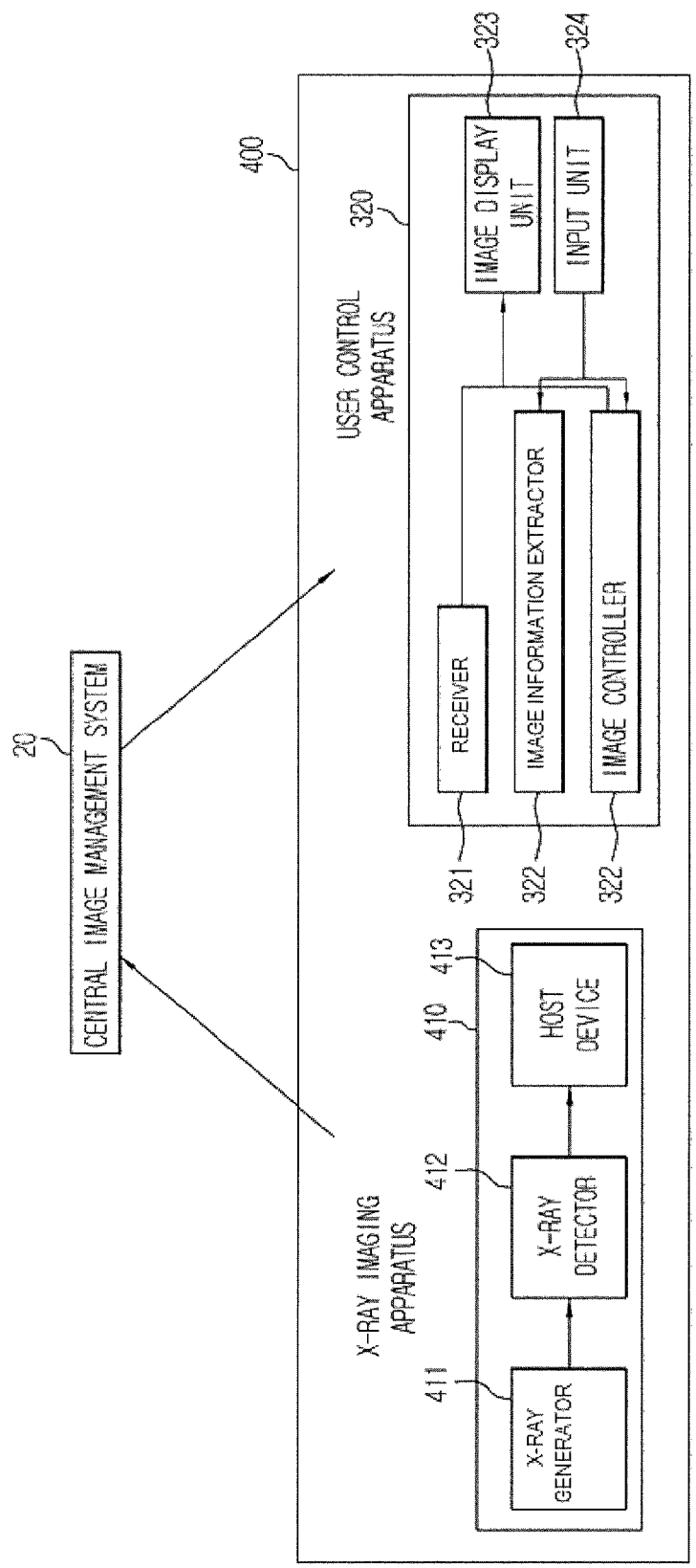
FIG. 13 is a control block diagram of an X-ray imaging system according to one or more embodiments.

FIG. 13 is a control block diagram of an X-ray imaging system 400 according to another embodiment of the present invention.

Referring to FIG. 13, the X-ray imaging system 400 may include an X-ray imaging apparatus 410 to generate a first energy X-ray image and a second energy X-ray image and to transmit the first energy X-ray image and the second energy X-ray image to the central image management system 20 or a user control apparatus 420, and the user control apparatus 420 to receive the first energy X-ray image and the second energy X-ray image from the central image management system 20 or the X-ray imaging apparatus 410, to select at least one region of the first energy X-ray image and the second energy X-ray image, and to generate and display a bone or soft tissue image corresponding to the selected region.

The X-ray imaging apparatus 410 is the same as the X-ray imaging apparatus 310 of FIG. 12, and thus, a detailed description thereof is omitted here.

The user control apparatus 420 may include a receiver 421 to receive the first energy X-ray image and the second energy X-ray image, an image display unit 424 to display at least one of the first energy X-ray image and the second energy X-ray image, an image information extractor 422 to extract bone image information and soft tissue image information from the first energy X-ray image and the second energy X-ray image, an input unit 425 to receive at least one region of the X-ray image displayed on the display unit 424, and an image controller 423 to generate one image containing the bone image information and the soft tissue image information.

When the image display unit 424 displays at least one of the first energy X-ray image and the second energy X-ray image which are received from the central image management system 20 or the X-ray imaging apparatus 410, the user may input user selection of at least one of the X-ray image displayed on the display unit 424 through the input unit 425.

The user control apparatus 320 described with reference to FIG. 11 may separately generate and display the bone or soft tissue image corresponding to the selected region. However, according to one or more embodiments, the user control apparatus 420 may generate and display one image obtained by combining the bone and soft tissue images corresponding to the selected region selected by the image controller 423.

In detail, the image information extractor 422 may extract the bone image information and the soft tissue image information corresponding to an entire X-ray image or the selected image. The image controller 423 may generate one image containing both the bone image information and the soft tissue image information with respect to the selected region and may display the one image on the image display unit 424. The one image may be an X-ray image that indicates both bones and soft tissues.

Figure 14A:
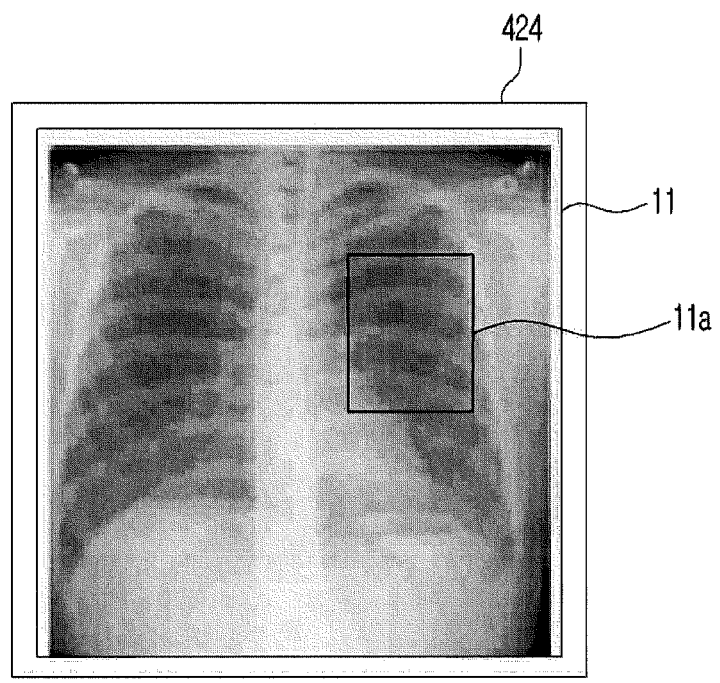
FIGS. 14A to 14C are diagrams showing images displayed on an image display unit of an X-ray imaging system, according to one or more embodiments.
Figure 14B:
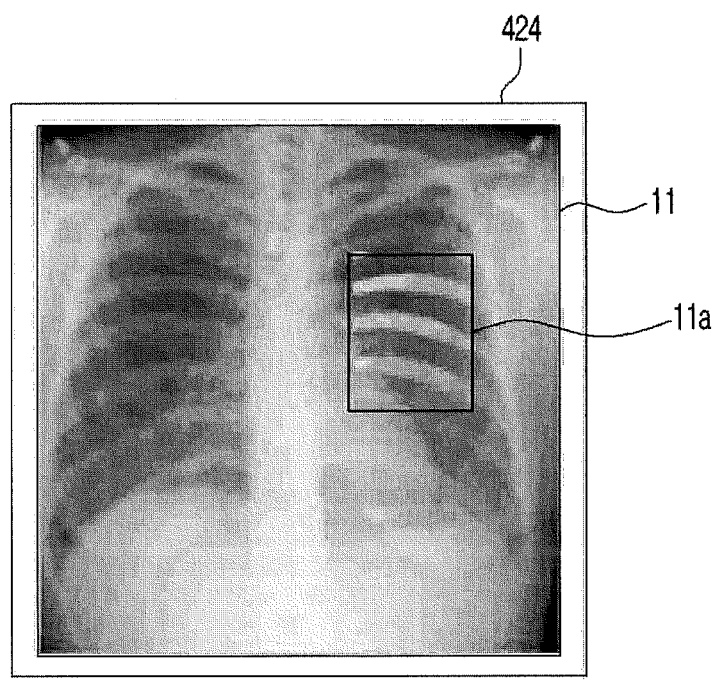
Figure 14C:
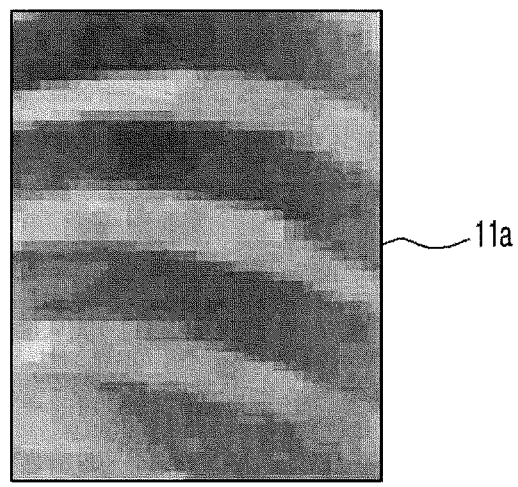

FIGS. 14A to 14C are diagrams showing images displayed on an image display unit, such as the image display unit 424 of the X-ray imaging system 400, according to one or more embodiments.

As shown in FIG. 14A, the image display unit 424 may display the first energy X-ray image. The user may select a region that is suspected to have a lesion or a region that is to be viewed by the user in more detail from the first energy X-ray image through the input unit 425.

When the user selection is input, one image containing both the bone and soft tissue image information corresponding to the selected region may be displayed, as shown in FIGS. 14B and 14C. In this case, the one image may replace the selected region and may be displayed, as shown in FIG. 14B. Alternatively, the one image may be enlarged and displayed on an entire screen of the image display unit 424, as shown in FIG. 14C.

The user may set the size of the one image through the input unit 425. Thus, the size of the one image displayed on the image display unit 424 may be adjusted according to the user setting.

When the image controller 423 generates the image containing the bone image information and the soft tissue image information, the image controller 423 may adjust bone and soft tissue regions of the image to exhibit different brightness levels such that the bones and the soft tissues may be distinguished from each other.

To this end, according to one or more embodiments, the image controller 423 may adjust pixel values corresponding to the bone or soft tissue region of the image containing the bone image information and the soft tissue image information such that the bone region and the soft tissue region may exhibit different brightness levels. In this case, a lighter region of the bone region and the soft tissue region may be optionally set by the image controller 423 or may be determined by user selection input to the input unit 425.

According to one or more embodiments, the image controller 423 may adjust any one of the bone region and the soft tissue region to be lighter or darker than the other such that the bone region and the soft tissue region may exhibit at different brightness levels. That is, the image controller 423 may adjust the bone region and the soft tissue region to be lighter or darker than each other.

In addition, when the image controller 423 generates the image containing the bone image information and the soft tissue image information, the image controller 423 may map the bone region and the soft tissue region to different color channels, respectively, so as to distinguish the bone image and the soft tissue image from each other.

The image controller 423 may map the bone region corresponding to the bone image information and the soft tissue region corresponding to the soft tissue image information to the different color channels, respectively. According to one or more embodiments, any color model may be used such that the color model includes at least two colors, and thus, the type of the color model is not particularly limited.

For example, with regard to a RGB model, the image controller 423 may map the bone image information and the soft tissue image information to a red channel and a green channel, respectively, and may generate and output the one image containing the bone image information and the soft tissue image information. Thus, the bone region and the soft tissue region of the image may be displayed red and green, respectively, so as to be distinguished from each other.

Respective colors mapped to the bone image information and the soft tissue image information may be input through the input unit 425 and may be optionally set by the image controller 423.

An example of an image displayed on the image display unit 424 in a case in which the image controller 423 maps the bone region and the soft tissue region to different color channels is shown in FIG. 9.

In the X-ray imaging systems 300 and 400 according to one or more embodiments, the X-ray imaging apparatuses 310 and 410 may reduce workload by not generating separate bone and soft tissue images and the central image management system 20 may reduce the burden imposed on server capacity by not storing the bone image and the soft tissue image. In addition, the user may check the bone image or the soft tissue image corresponding to a desired region only, instead of the entire all a high energy X-ray image, the bone image, and the soft tissue image, thereby possibly reducing diagnosis time or fatigue.

Hereinafter, a method of controlling an X-ray imaging apparatus will be described with regard to one or more embodiments.

Figure 15:
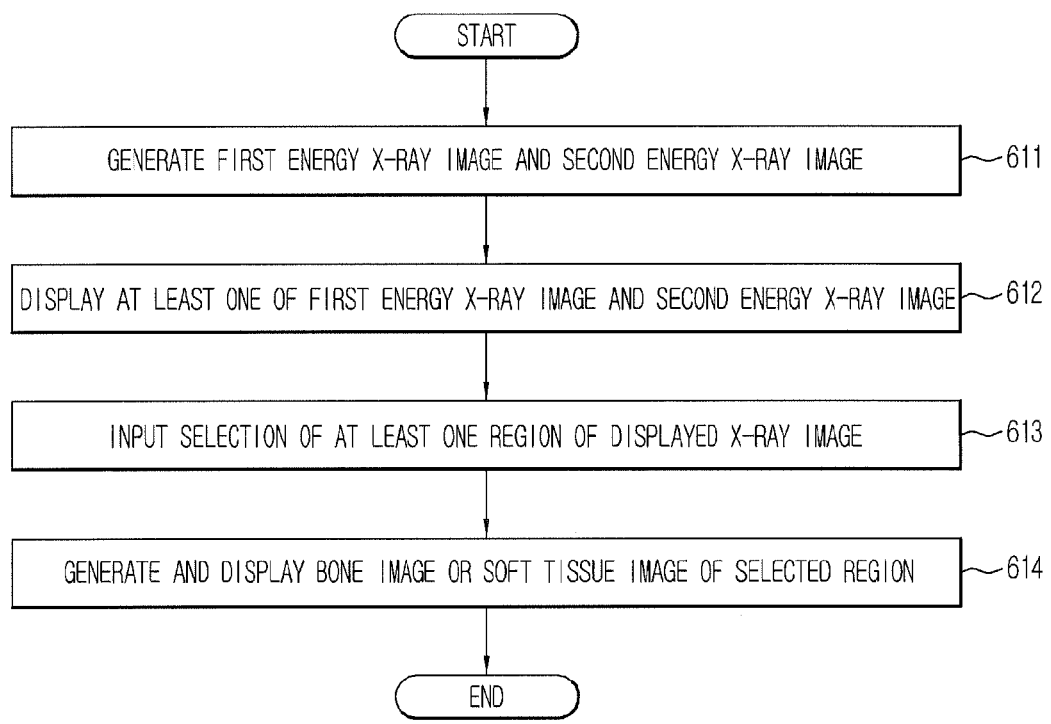
FIG. 15 is a flowchart of a method of controlling an X-ray imaging apparatus according to one or more embodiments.

FIG. 15 is a flowchart of a method of controlling an X-ray imaging apparatus according to one or more embodiments.

Referring to FIG. 15, a first energy X-ray image and a second energy X-ray image may be generated (611). First energy and second energy may have different energy levels. First energy X-rays may be irradiated and detected to generate the first energy X-ray image and second energy X-rays may be irradiated and detected to generate the second energy X-ray image. Alternatively, the first energy X-ray image and the second energy X-ray image may be generated by irradiating and detecting X-rays with a predetermined energy level and then extracting the first energy X-rays and the second energy X-rays from the detected X-rays.

At least one of the first energy X-ray image and the second energy X-ray image may be displayed (612). That is, only one of the first energy X-ray image and the second energy X-ray image may be displayed or both the first energy X-ray image and the second energy X-ray image may be displayed, if necessary. In general, a high energy X-ray image may be displayed and used for diagnosis but embodiments are not limited thereto.

Selection of at least one region of the displayed X-ray image may be input (613). The selected region may have a predetermined area and the shape or size of the selected region is not particularly limited.

In addition, a bone or soft tissue image corresponding to the selected region may be generated and displayed (614). Here, the bone image may contain bone image information and indicates bones. The soft tissue image may contain soft tissue image information and indicates soft tissues.

A method of displaying the bone image or the soft tissue image may include a method of replacing only the selected region with the bone image or the soft tissue image and a method of enlarging the size of the bone image or the soft tissue image. Here, the size of the bone image or the soft tissue image may be optionally adjusted or may be adjusted according to user setting.

Figure 16:
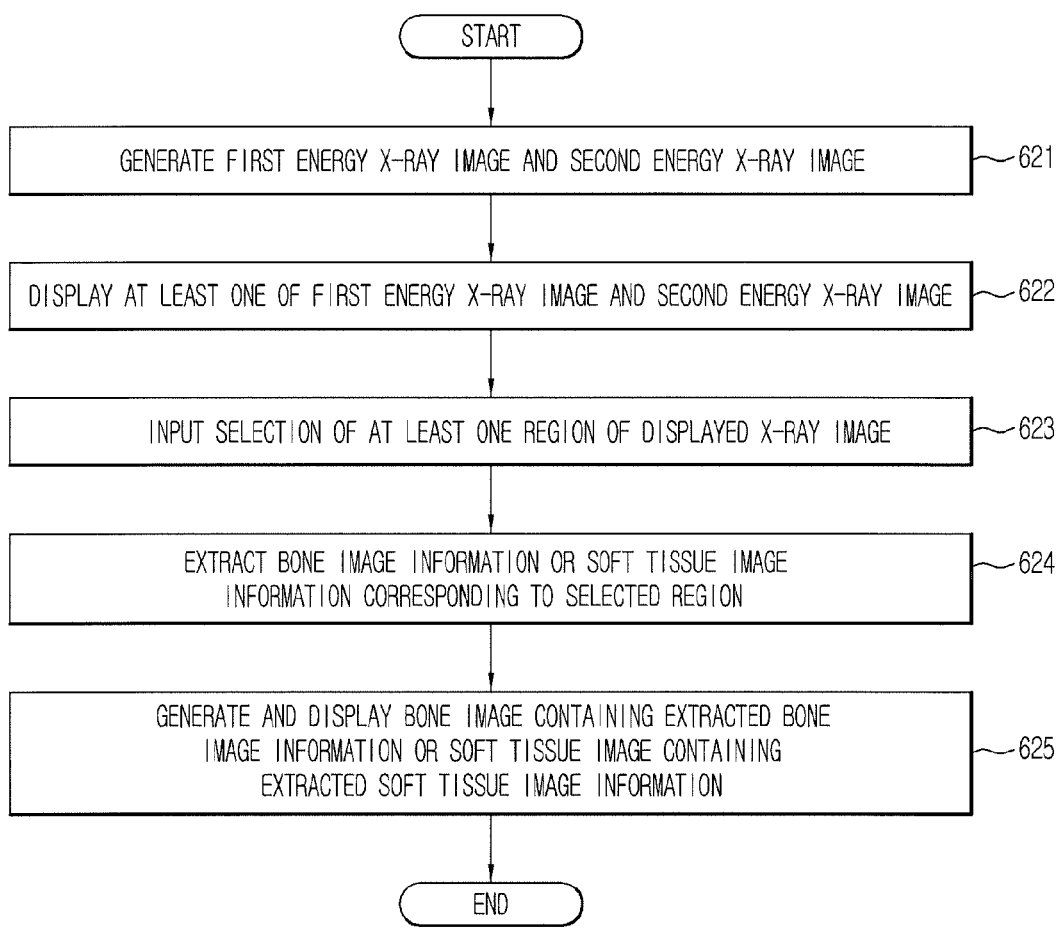
FIG. 16 is a flowchart of a method of controlling an X-ray imaging apparatus that extracts bone or soft tissue image information corresponding to a selected region only according to one or more embodiments.

FIG. 16 is a flowchart of a method of controlling an X-ray imaging apparatus that extracts bone or soft tissue image information corresponding to a selected region only, according to one or more embodiments.

Referring to FIG. 16, a first energy X-ray image and a second energy X-ray image may be generated (621) and at least one of the first energy X-ray image and the second energy X-ray image may be displayed (622). These operations are the same as in FIG. 15, and thus, a detailed description thereof is omitted here.

Selection of at least one region of the displayed X-ray image may be input (623). When the selection is input, the bone image information or soft tissue image information corresponding to the selected region may be extracted (624). The extraction of the bone or soft tissue image information has been described above in the detailed description of the X-ray imaging apparatus and the X-ray imaging system, and thus, a detailed description thereof will be omitted here.

A bone image containing the extracted bone image information or a soft tissue image containing the extracted soft tissue image information may be generated and displayed (625). Here, a method of displaying the bone image or the soft tissue image is referred to with reference to FIG. 16.

Figure 17:
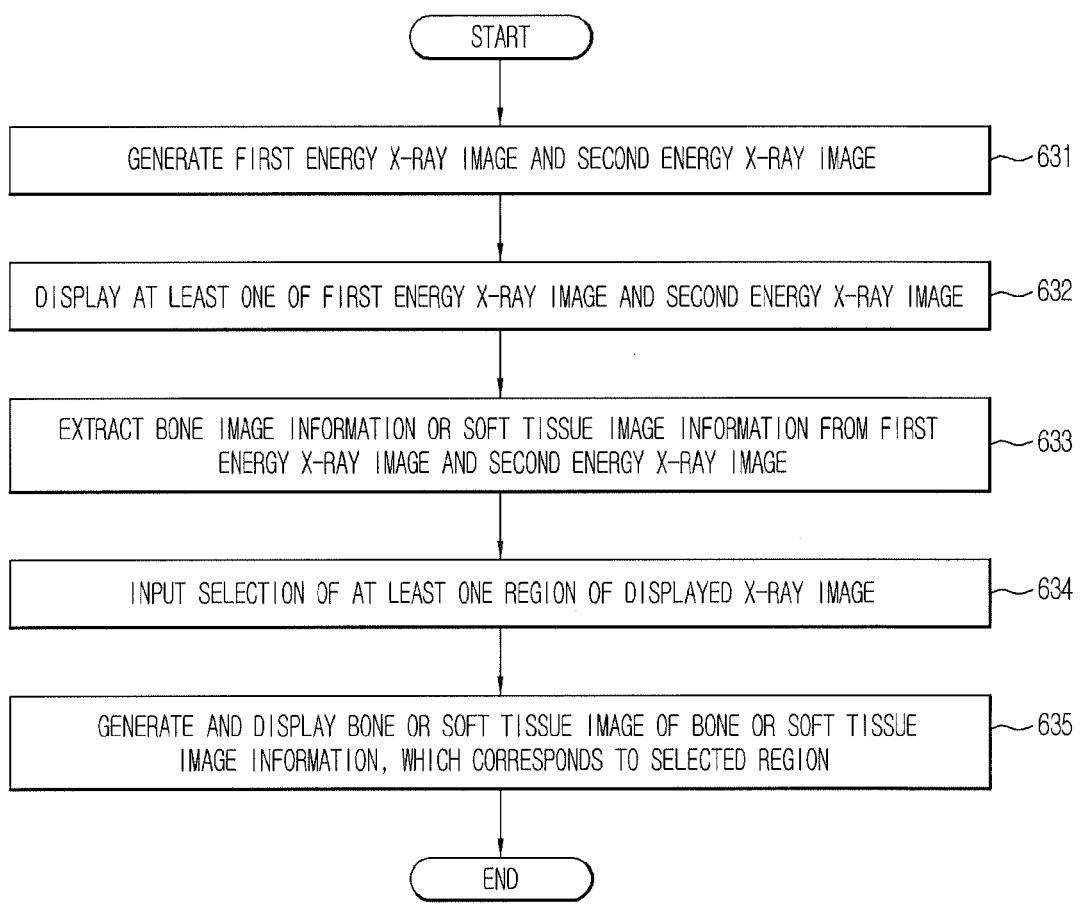
FIG. 17 is a flowchart of a method of controlling an X-ray imaging apparatus that extracts bone image information or soft tissue image information regardless of user selection according to one or more embodiments.

FIG. 17 is a flowchart of a method of controlling an X-ray imaging apparatus that extracts bone image information or soft tissue image information regardless of user selection according to one or more embodiments.

Referring to FIG. 17, a first energy X-ray image and a second energy X-ray image may be generated (631) and at least one of the first energy X-ray image and the second energy X-ray image may be displayed (632).

In addition, bone image information or soft tissue image information may be extracted from the first energy X-ray image and the second energy X-ray image (633). That is, the bone image information or the soft tissue image information may be extracted from an entire X-ray image, but not from a selected region.

Selection of at least one region of the selected X-ray image may be input (634).

When the selection is input, a bone or soft tissue image containing information of the bone image information or the soft tissue image information, which corresponds to the selected region, may be generated and displayed (635). Here, a method of displaying the bone image or the soft tissue image is referred to with reference to FIG. 16.

Figure 18:
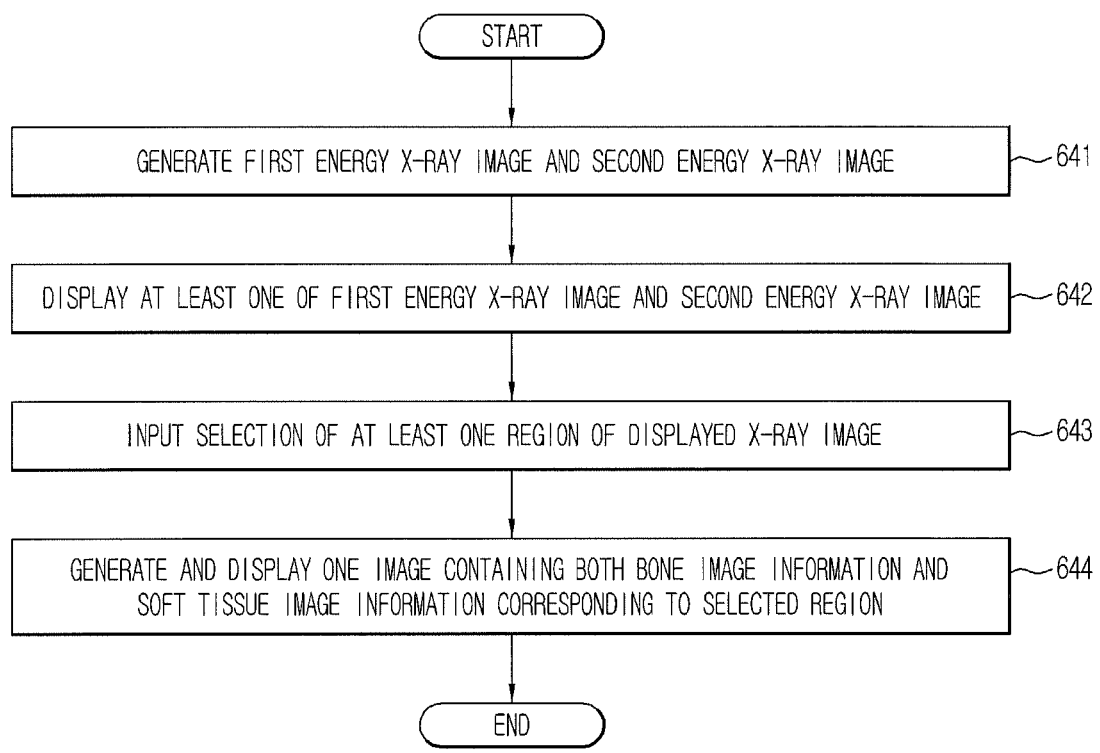
FIG. 18 is a flowchart of a method of controlling an X-ray imaging apparatus according to one or more embodiments.

FIG. 18 is a flowchart of a method of controlling an X-ray imaging apparatus according to one or more embodiments.

Referring to FIG. 18, a first energy X-ray image and a second energy X-ray image may be generated (641) and at least one of the first energy X-ray image and the second energy X-ray image may be displayed (642). Here, a method of generating the first energy X-ray image and the second energy X-ray image may be the same as in the above-described embodiments, and thus, a detailed description thereof is omitted here.

Selection of at least one region of the displayed X-ray region may be input (643).

When the selection is input, one image containing both bone and soft tissue image information corresponding to a selected region may be generated and displayed (644).

In detail, the bone image information and soft tissue image information corresponding to the selected region may be extracted from the first energy X-ray image and the second energy X-ray image, and the one image containing both the bone image information and the soft tissue image information may be generated and displayed.

Alternatively, the bone image information and soft tissue image information corresponding to an entire image may be extracted from the first energy X-ray image and the second energy X-ray image, and the one image containing both the bone image information and soft tissue image information of the extracted information, which correspond to the selected region, may be generated and displayed.

An operation of generating the one image containing both the bone image information and the soft tissue image information may include an operation of adjusting brightness levels of a bone region and a soft tissue region of the one image and displaying the one image or an operation of mapping the bone region and the soft tissue region of the one image to different color channels and displaying the one image.

In addition, the one image may replace the selected region, may be enlarged and displayed, or the size of the selected region may be selected according to user setting.

Hereinafter, a method of controlling an X-ray imaging system will be described with regard to one or more embodiments.

Figure 19:
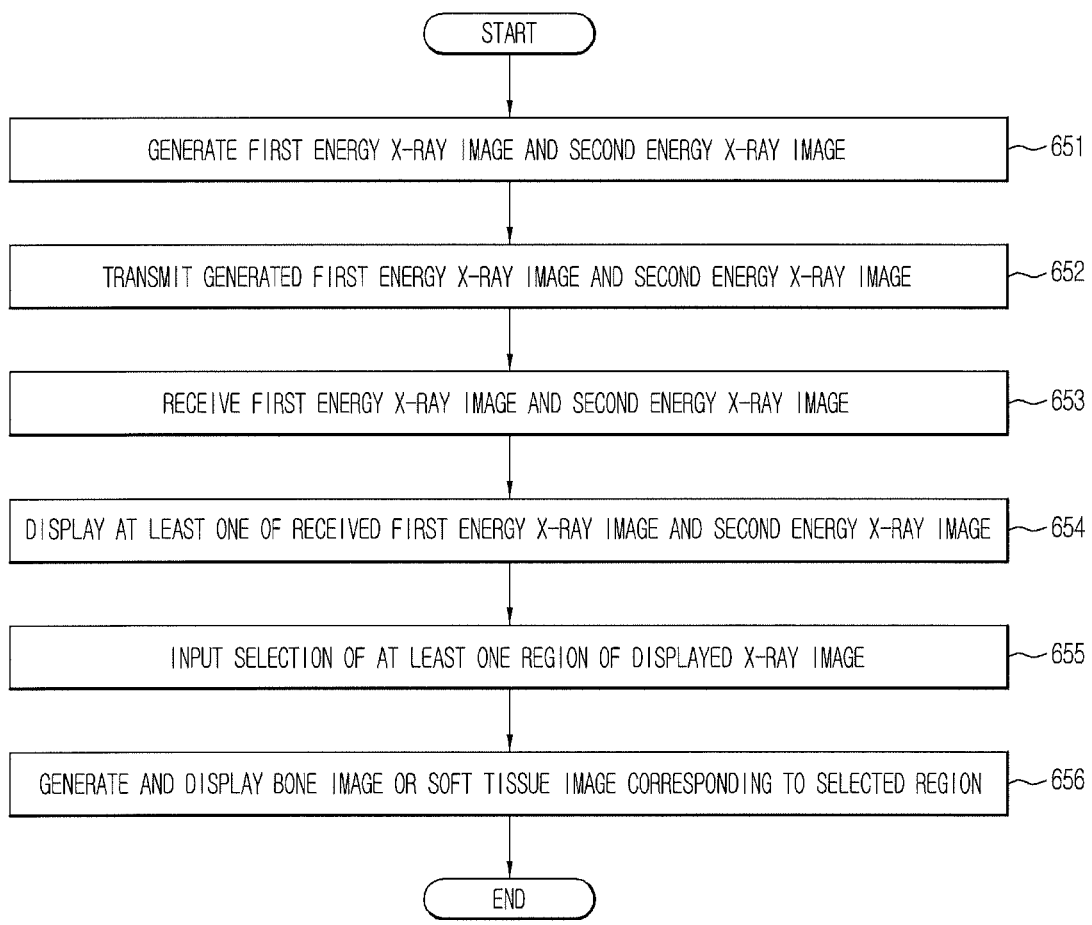
FIG. 19 is a flowchart of a method of controlling an X-ray imaging system according to one or more embodiments.

FIG. 19 is a flowchart of a method of controlling an X-ray imaging system according to one or more embodiments.

Referring to FIG. 19, an X-ray imaging apparatus may generate a first energy X-ray image and a second X-ray image (651). A method of generating an X-ray image is the same as in the above-described embodiments.

The first energy X-ray image and the second energy X-ray image may be transmitted to the central image management system 20 (652). In this case, the first energy X-ray image and the second energy X-ray image may be transmitted directly to a user control apparatus.

The user control apparatus may receive the first energy X-ray image and the second energy X-ray image (653). Here, the first energy X-ray image and the second energy X-ray image may be received by downloading the images according to a request to the central image management system 20 or may be received directly from the X-ray imaging apparatus.

The user control apparatus may display at least one of the first energy X-ray image and the second energy X-ray image (654).

Selection of at least one region of the displayed X-ray image may be input (655) and a bone or soft tissue image corresponding to a selected region may be generated and displayed (656).

Figure 20:
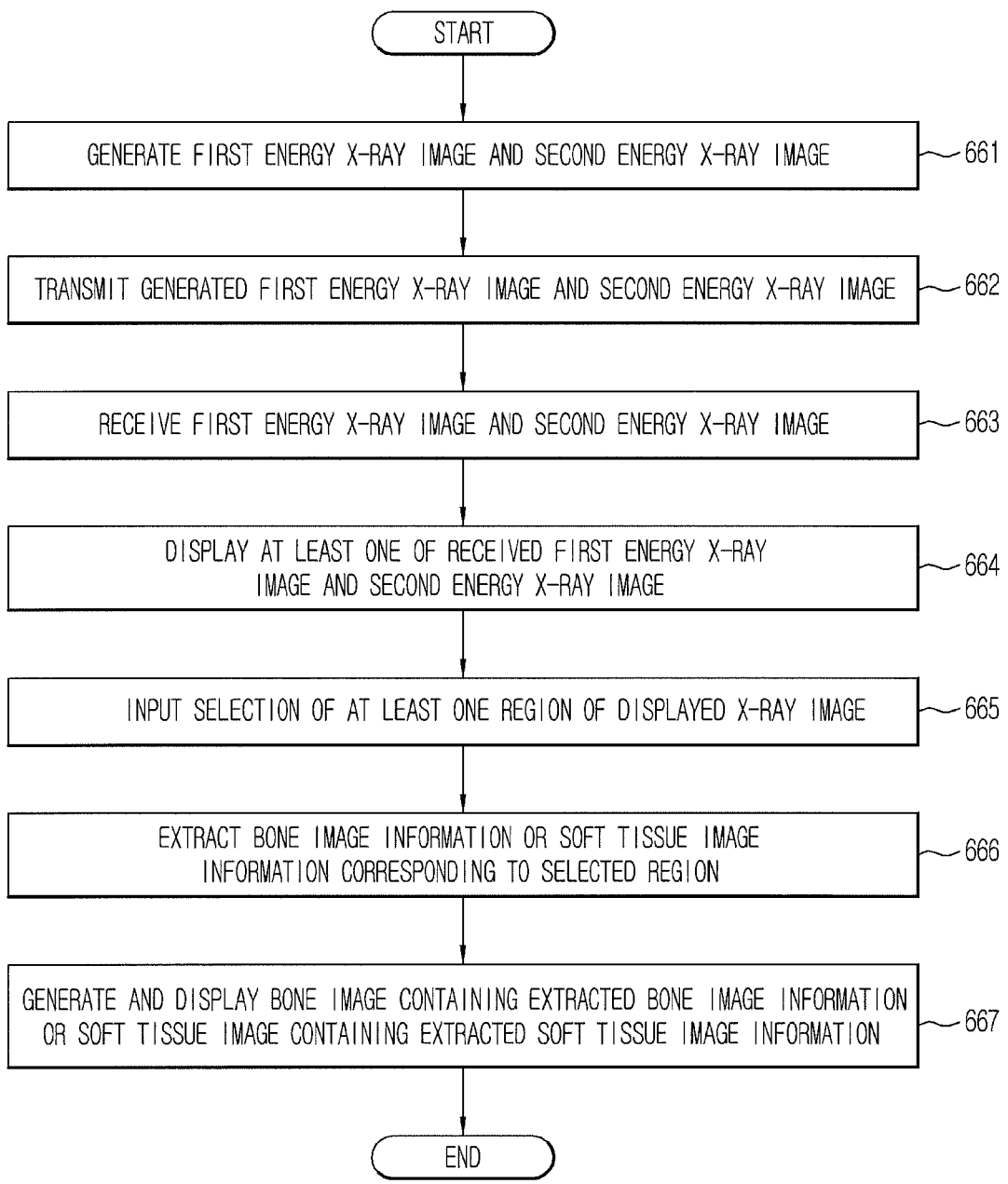
FIG. 20 is a flowchart of a method of controlling an X-ray imaging system that extracts bone or soft tissue image information corresponding to a selected region only according to one or more embodiments.

FIG. 20 is a flowchart of a method of controlling an X-ray imaging system that extracts bone or soft tissue image information corresponding to a selected region only, according to one or more embodiments.

Referring to FIG. 20, an X-ray imaging apparatus may generate a first energy X-ray image and a second X-ray image (661) and may transmit the first energy X-ray image and the second energy X-ray image to the central image management system 20 (662), or alternatively, may transmit the images directly to a user control apparatus.

The user control apparatus may receive the first energy X-ray image and the second energy X-ray image (663) and may display at least one of the first energy X-ray image and the second energy X-ray image on an image display unit (664).

Selection of at least one region of the displayed X-ray image may be input (665) and bone or soft tissue image information corresponding to the selected region may be extracted when the selection is input (666).

A bone image containing the bone image information or a soft tissue image containing the soft tissue image information may be generated and displayed (667).

Figure 21:
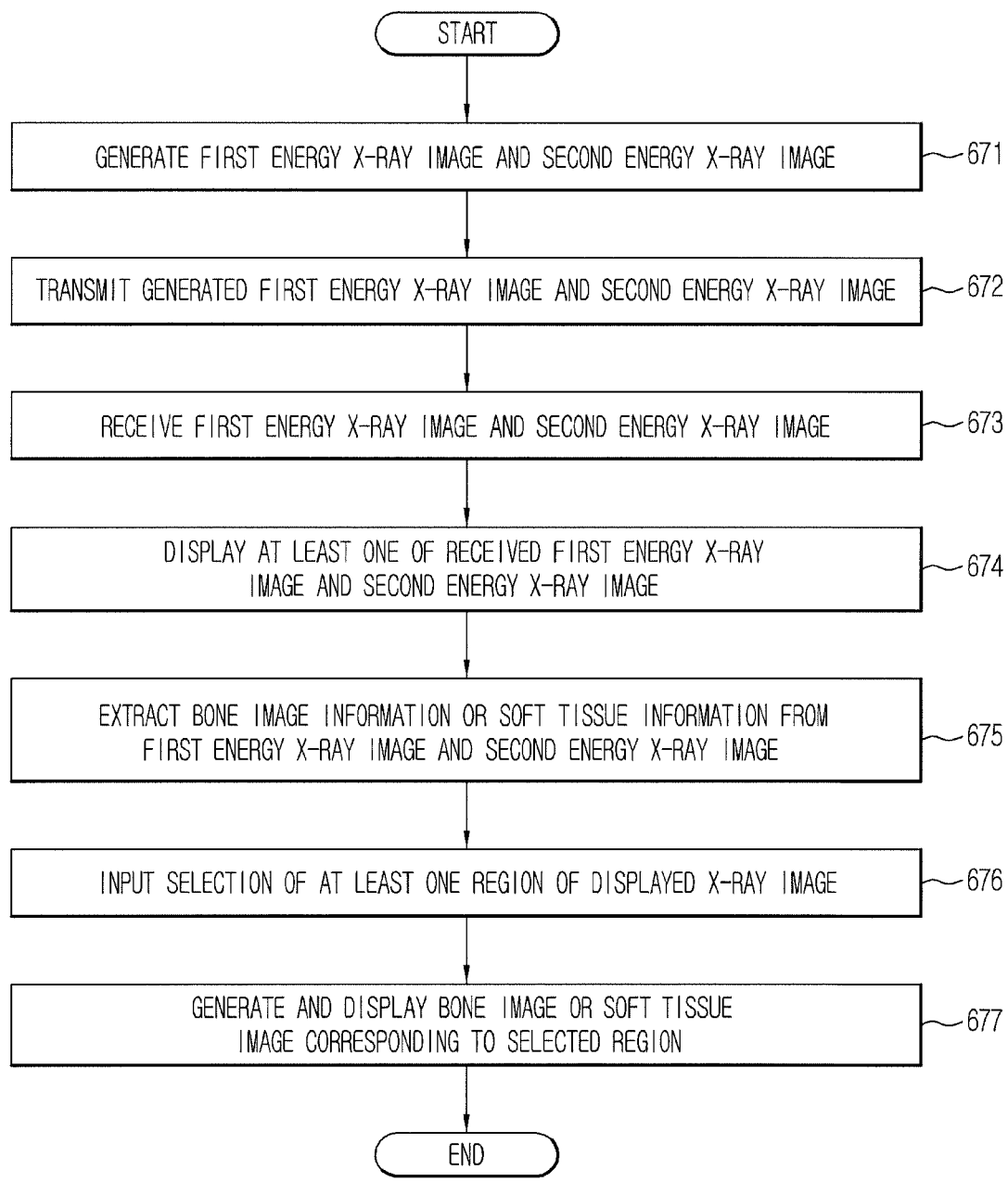
FIG. 21 is a flowchart of a method of controlling an X-ray imaging system that extracts bone image information or soft tissue image information regardless of user selection according to one or more embodiments.

FIG. 21 is a flowchart of a method of controlling an X-ray imaging system that extracts bone image information or soft tissue image information regardless of user selection, according to one or more embodiments.

Referring to FIG. 21, an X-ray imaging apparatus may generate a first energy X-ray image and a second X-ray image (671) and may transmit the first energy X-ray image and the second energy X-ray image to the central image management system 20 (672), or alternatively, may transmit the images directly to a user control apparatus.

The user control apparatus may receive the first energy X-ray image and the second energy X-ray image (673) and may display at least one of the first energy X-ray image and the second energy X-ray image (674).

Bone image information or soft tissue image information may be extracted from the first energy X-ray image and the second energy X-ray image (675). That is, the bone or soft tissue image information corresponding to an entire X-ray image instead of a selected region may be extracted.

Selection of at least one region of the displayed X-ray image may be input (676).

When the selection is input, a bone or soft tissue image containing information of the bone image information or the soft tissue image information, which corresponds to the selected region, may be generated and displayed (677).

Figure 22:
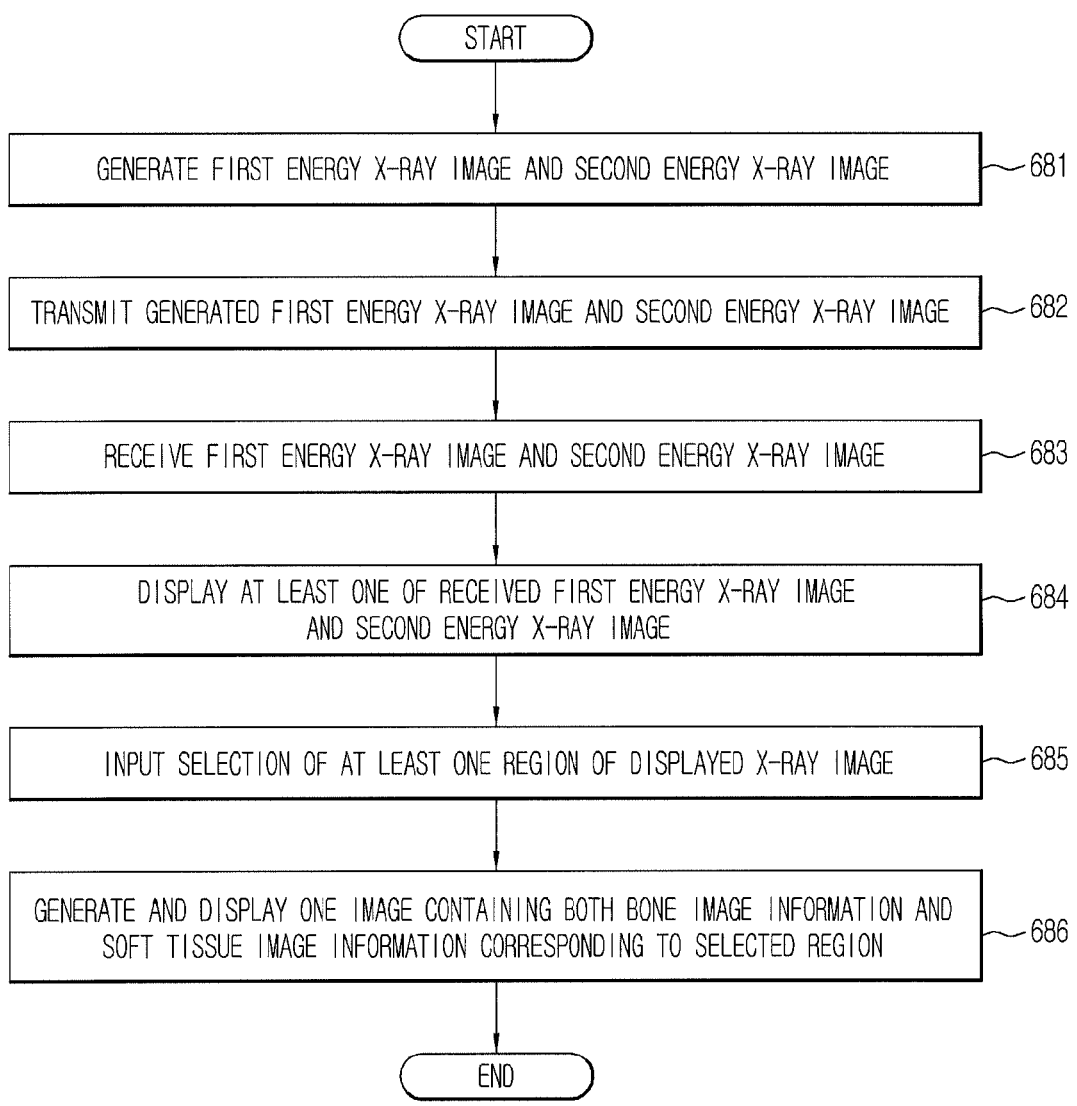
FIG. 22 is a flowchart of a method of controlling an X-ray imaging system according to one or more embodiments.

FIG. 22 is a flowchart of a method of controlling an X-ray imaging system according to one or more embodiments.

Referring to FIG. 22, an X-ray imaging apparatus may generate a first energy X-ray image and a second X-ray image (681) and may transmit the first energy X-ray image and the second X-ray image to the central image management system 20 (682), or alternatively, may transmit the images directly to a user control apparatus.

The user control apparatus may receive the first energy X-ray image and second energy X-ray image (683) and may display at least one of the first energy X-ray image and the second energy X-ray image on an image display unit (684).

Selection of at least region of the displayed X-ray image may be input (685) and one image containing bone and soft tissue image information corresponding to a selected region may be generated and displayed (686).

In detail, the bone and the soft tissue image information corresponding to the selected region may be extracted from the first energy X-ray image and the second energy X-ray image and the one image containing both the bone image information and the soft tissue image information may be generated and displayed.

Alternatively, the bone and the soft tissue image information corresponding to an entire image may be extracted from the first energy X-ray image and the second energy X-ray image and the one image containing both the bone and soft tissue image information of the extracted information, which corresponds to the selected region, may be generated and displayed.

An operation of generating the one image containing both the bone image information and the soft tissue image information may include an operation of adjusting brightness levels of a bone region and a soft tissue region of the one image and displaying the one image or an operation of mapping the bone region and the soft tissue region of the one image to different color channels and displaying the one image.

In addition, the one image may replace the selected region, may be enlarged and displayed, or the size of the selected region may be determined according to user setting.

As is apparent from the above description, an X-ray imaging apparatus according to one or more embodiments may display a bone or soft tissue image, which corresponds to a region selected by a user, thereby reducing diagnosis time.

In addition, in an X-ray imaging system according to one or more embodiments, a first energy X-ray image and a second energy X-ray image may be transmitted to a central image management system, a user control apparatus may receive the images from the central image management system, and a bone or soft tissue image corresponding to the selected region may be displayed, thereby possibly reducing burden imposed on server capacity of the central image management system as well as diagnosis time.

In one or more embodiments, any apparatus, system, element, or interpretable unit descriptions herein include one or more hardware devices or hardware processing elements. For example, in one or more embodiments, any described apparatus, system, element, retriever, pre or post-processing elements, tracker, detector, encoder, decoder, etc., may further include one or more memories and/or processing elements, and any hardware input/output transmission devices, or represent operating portions/aspects of one or more respective processing elements or devices. Further, the term apparatus should be considered synonymous with elements of a physical system, not limited to a single device or enclosure or all described elements embodied in single respective enclosures in all embodiments, but rather, depending on embodiment, is open to being embodied together or separately in differing enclosures and/or locations through differing hardware elements.

In addition to the above described embodiments, embodiments can also be implemented through computer readable code/instructions in/on a non-transitory medium, e.g., a computer readable medium, to control at least one processing device, such as a processor or computer, to implement any above described embodiment. The medium can correspond to any defined, measurable, and tangible structure permitting the storing and/or transmission of the computer readable code.

The media may also include, e.g., in combination with the computer readable code, data files, data structures, and the like. One or more embodiments of computer-readable media include: magnetic media such as hard disks, floppy disks, and magnetic tape; optical media such as CD ROM disks and DVDs; magneto-optical media such as optical disks; and hardware devices that are specially configured to store and perform program instructions, such as read-only memory (ROM), random access memory (RAM), flash memory, and the like. Computer readable code may include both machine code, such as produced by a compiler, and files containing higher level code that may be executed by the computer using an interpreter, for example. The media may also be any defined, measurable, and tangible distributed network, so that the computer readable code is stored and executed in a distributed fashion. Still further, as only an example, the processing element could include a processor or a computer processor, and processing elements may be distributed and/or included in a single device.

The computer-readable media may also be embodied in at least one application specific integrated circuit (ASIC) or Field Programmable Gate Array (FPGA), as only examples, which execute (e.g., processes like a processor) program instructions.

While aspects of the present invention has been particularly shown and described with reference to differing embodiments thereof, it should be understood that these embodiments should be considered in a descriptive sense only and not for purposes of limitation. Descriptions of features or aspects within each embodiment should typically be considered as available for other similar features or aspects in the remaining embodiments. Suitable results may equally be achieved if the described techniques are performed in a different order and/or if components in a described system, architecture, device, or circuit are combined in a different manner and/or replaced or supplemented by other components or their equivalents.

Thus, although a few embodiments have been shown and described, with additional embodiments being equally available, it would be appreciated by those skilled in the art that changes may be made in these embodiments without departing from the principles and spirit of the invention, the scope of which is defined in the claims and their equivalents.

What is claimed is:

1. An X-ray imaging apparatus comprising:
an X-ray generator to generate X-rays and irradiate an object with the X-rays;
an X-ray detector to detect X-rays irradiated from the X-ray generator and transmitted through the object; and
a host device to generate and display at least one of X-ray images from the detected X-rays, to extract at least one of bone image information and soft tissue image information corresponding only to a region selected by a user from the X-ray images when selection of the region of the displayed X-ray image is input from the user and to display an image containing the at least one of bone image information and soft tissue image information of the displayed X-ray image.

2. The X-ray imaging apparatus according to claim 1, wherein the X-ray detector detects first energy X-rays and second energy X-rays, wherein the first energy X-rays and the second energy X-rays have different energy levels.

3. The X-ray imaging apparatus according to claim 2, wherein the host device comprises an X-ray image generator to generate a first energy X-ray image from the first energy X-rays detected by the X-ray detector and to generate a second energy X-ray image from the second energy X-rays detected by the X-ray detector.

4. The X-ray imaging apparatus according to claim 3, wherein the host device further comprises an image display unit to display at least one of the first energy X-ray image and second energy X-ray image generated by the X-ray image generator.

5. The X-ray imaging apparatus according to claim 4, wherein the host device further comprises an image information extractor to extract a bone image and a soft tissue image from the first energy X-ray image and the second energy X-ray image to extract the bone image information or the soft tissue image information.

6. The X-ray imaging apparatus according to claim 5, wherein the host device further comprises an input unit to receive, from the user, selection of at least one region of the image displayed on the image display unit.

7. The X-ray imaging apparatus according to claim 6, wherein the image information extractor extracts bone image information or soft tissue image information corresponding to the region selected by the user.

8. The X-ray imaging apparatus according to claim 6, wherein the image display unit displays the bone image or soft tissue image corresponding to the region selected by the user, and
wherein the bone image contains the bone image information generated by the image information extractor and the soft tissue image contains the soft tissue image information generated by the image information extractor.

9. The X-ray imaging apparatus according to claim 8, wherein the image display unit replaces the selected region of the displayed X-ray image with an image containing image information extracted by the image information extractor and displays the selected region.

10. The X-ray imaging apparatus according to claim 6, wherein the input unit receives selection of at least one of bones and soft tissues from the user, and
wherein the image information extractor extracts image information corresponding to the selection.

11. The X-ray imaging apparatus according to claim 6, wherein the image information extractor further comprises an image controller to generate one image containing both the bone image information and soft tissue image information of the image information extracted by the image information extractor, the bone image information and soft tissue image information corresponding to the selected region, wherein the selected region is selected via the input unit, and
wherein the one image comprises a bone region corresponding to the bone image information and a soft tissue region corresponding to the soft tissue image information.

12. The X-ray imaging apparatus according to claim 11, wherein the image controller adjusts the bone region and soft tissue region included in the one image to different brightness levels.

13. The X-ray imaging apparatus according to claim 11, wherein the image controller maps the bone region and soft tissue region included in the one image to different colors.

14. The X-ray imaging apparatus according to claim 11, wherein the image display unit displays the one image generated by the image controller.

15. The X-ray imaging apparatus according to claim 14, wherein the image display unit replaces the selected region of the displayed X-ray image with the one image generated by the image controller.

16. An X-ray imaging system comprising:
an X-ray imaging apparatus to transmit and receive an X-ray image to and from a central image management system; and
a user control apparatus,
wherein the X-ray imaging apparatus irradiates an object with X-rays, detects X-rays transmitted through the object to generate a plurality of X-ray images, and transmits the X-ray images to the central image management system, and
wherein the user control apparatus receives the X-ray images from the central image management system, displays the X-ray images, extracts at least one of bone image information and soft tissue image information corresponding only to a region selected by a user from the X-ray images when selection of the region of the displayed X-ray image is input from the user and displays an image containing at least one of the bone image information and the soft tissue image information.

17. The X-ray imaging system according to claim 16, wherein the X-ray imaging apparatus irradiates the object with a first energy X-ray and second energy X-ray having different energy levels, detects the first and second energy X-rays, and generates a first energy X-ray image from the first energy X-ray and a second energy X-ray image from the second energy X-ray.

18. The X-ray imaging system according to claim 17, wherein the user control apparatus comprises an image display unit to receive the first energy X-ray image and second energy X-ray image generated by the X-ray imaging apparatus and to display at least one of the first energy X-ray image and the second energy X-ray image.

19. The X-ray imaging system according to claim 18, wherein the user control apparatus further comprises an image information extractor to extract a bone image and a soft tissue image from the first energy X-ray image and the second energy X-ray image to extract bone image information or soft tissue image information.

20. The X-ray imaging system according to claim 19, wherein the user control apparatus further comprises an input unit to receive, from the user, selection of at least one region of the image displayed on the image display unit.

21. The X-ray imaging system according to claim 20, wherein the input unit receives selection of at least one of bones and soft tissues from the user, and
wherein the image information extractor extracts image information corresponding to the selection.

22. The X-ray imaging system according to claim 20, wherein the image information extractor extracts bone image information or soft tissue image information corresponding to the region selected by the user.

23. The X-ray imaging system according to claim 22, wherein the image display unit displays the bone image or soft tissue image corresponding to the region selected by the user, and
wherein the bone image contains the bone image information generated by the image information extractor and the soft tissue image contains the soft tissue image information generated by the image information extractor.

24. The X-ray imaging system according to claim 23, wherein the image display unit replaces the selected region of the displayed X-ray image with an image containing image information extracted from the image information extractor and displays the selected region.

25. The X-ray imaging system according to claim 23, wherein the image information extractor further comprises an image controller to generate one image containing both the bone image information and soft tissue image information of the image information extracted by the image information extractor, the bone image information and soft tissue image information corresponding to the selected region, wherein the selected region is selected via the input unit, and
wherein the one image comprises a bone region corresponding to the bone image information and a soft tissue region corresponding to the soft tissue image information.

26. The X-ray imaging system according to claim 25, wherein the image controller adjusts the bone region and soft tissue region included in the one image to different brightness levels.

27. The X-ray imaging system according to claim 25, wherein the image controller maps the bone region and soft tissue region included in the one image to different colors.

28. The X-ray imaging system according to claim 25, wherein the image display unit displays the one image generated by the image controller.

29. The X-ray imaging system according to claim 28, wherein the image display unit replaces the selected region of the displayed X-ray image with the one image generated by the image controller.

30. A method of controlling an X-ray imaging apparatus, the method comprising:
generating a first energy X-ray image and second energy X-ray image having different energy levels;
displaying at least one of the first energy X-ray image and the second energy X-ray image;
receiving selection of at least one region of the displayed X-ray image by a user;
extracting at least one of bone image information and soft tissue image information corresponding only to the at least one region selected by the user from the first energy X-ray image and the second energy X-ray image; and
generating and displaying an image containing the at least one of bone image information and soft tissue image information.

31. The method according to claim 30, wherein the generating of the first energy X-ray image and second energy X-ray image comprises generating an image containing image information of the extracted bone image information or the soft tissue image information, the image information corresponding to the region selected by a user.

32. The method according to claim 30, wherein the generating of the first energy X-ray image and second energy X-ray image comprises extracting the bone image information or soft tissue image information corresponding to the region selected by a user and generating an image containing the extracted bone image information or soft tissue image information.

33. The method according to claim 30, wherein the generating of the first energy X-ray image and second energy X-ray image comprises extracting bone image information and soft tissue image information from the first energy X-ray image and the second energy X-ray image and generating one image containing bone image information and soft tissue image information of the extracted bone image information and soft tissue image information, the bone image information and soft tissue image information corresponding to the region selected by the user.

34. The method according to claim 33 further comprising adjusting a bone region and a soft tissue region to different brightness levels.

35. The method according to claim 33, further comprising mapping a bone region and soft tissue region included in the one image to different color channels.

36. The method according to claim 30, wherein the generating of the first energy X-ray image and second energy X-ray image comprises extracting bone image information and soft tissue image information corresponding to the region selected by the user from the first energy X-ray image and the second energy X-ray image and generating one image containing the extracted bone image information and soft tissue image information.

37. A method of controlling an X-ray imaging system comprising an X-ray imaging apparatus to generate an X-ray image and a user control apparatus, the method comprising:
the X-ray imaging apparatus generating a first energy X-ray image and second energy X-ray image having different energy levels and transmitting the first energy X-ray image and the second energy X-ray image to a central image management system;
the user control apparatus receiving the first energy X-ray image and the second energy X-ray image from the central image management system and displaying at least one of the first energy X-ray image and the second energy X-ray image;
receiving selection of at least one region of the displayed X-ray image by a user;
extracting at least one of bone image information and soft tissue image information corresponding only to the at least one region selected by the user from the first energy X-ray image and the second energy X-ray image; and
generating and displaying the at least one of bone image information and soft tissue image information.

38. The method according to claim 37, wherein the generating of the first energy X-ray image and second energy X-ray image comprises extracting the bone image information or the soft tissue image information from the first energy X-ray image and the second energy X-ray image.

39. The method according to claim 38, wherein the generating of the first energy X-ray image and second energy X-ray image comprises generating an image containing image information of the extracted bone image information or soft tissue image information, the image information corresponding to the region selected by the user.

40. The method according to claim 37, wherein the generating of the first energy X-ray image and second energy X-ray image comprises extracting the bone image information or soft tissue image information corresponding to the region selected by the user and generating an image containing the extracted bone image information or soft tissue image information.

41. The method according to claim 37, wherein the generating of the first energy X-ray image and second energy X-ray image comprises extracting bone image information and soft tissue image information from the first energy X-ray image and the second energy X-ray image and generating one image containing bone image information and soft tissue image information of the extracted bone image information and the soft tissue image information, the bone image information and soft tissue image information corresponding to the region selected by the user.

42. The method according to claim 41, further comprising adjusting a bone region and a soft tissue region to different brightness levels.

43. The method according to claim 41, further comprising mapping a bone region and soft tissue region included in the one image to different color channels.

44. The method according to claim 37, wherein the generating of the first energy X-ray image and second energy X-ray image comprises extracting bone image information and soft tissue image information corresponding to the region selected by the user from the first energy X-ray image and the second energy X-ray image and generating one image containing the extracted bone image information and soft tissue image information.

45. A method of controlling an electro-magnetic radiation imaging apparatus, the method comprising:
 displaying at least one of a first energy electro-magnetic radiation image and a second energy electro-magnetic radiation image, the first energy electro-magnetic radiation image and the second energy electro-magnetic radiation image having different energy levels;
 receiving selection of at least one region of the displayed electro-magnetic radiation image by a user;
 extracting at least one of bone image information and soft tissue image information corresponding only to the at least one region selected by the user from the first energy electro-magnetic radiation image and the second energy electro-magnetic radiation image; and
 generating an image containing the at least one of the bone image information and the soft tissue image information.

46. The method according to claim 45, wherein the generating of the image comprises generating one image containing bone image information and soft tissue image information of the extracted bone image information and soft tissue image information.

47. The method according to claim 46 further comprising adjusting a bone region and a soft tissue region to different brightness levels.

48. The method according to claim 46, further comprising mapping a bone region and soft tissue region included in the one image to different color channels.

\* \* \* \* \*